(12) United States Patent
Payne et al.

(10) Patent No.: US 10,660,675 B2
(45) Date of Patent: *May 26, 2020

(54) EXTERNAL ADJUSTMENT DEVICE FOR DISTRACTION DEVICE

(71) Applicant: NuVasive Specialized Orthopedics Inc., San Diego, CA (US)

(72) Inventors: Timothy John Payne, Santa Ana, CA (US); Kevin Oberkramer, Placentia, CA (US); Scott Pool, Laguna Hills, CA (US); Arvin Chang, Yorba Linda, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/046,916

(22) Filed: Jul. 26, 2018

(65) Prior Publication Data
US 2019/0000515 A1    Jan. 3, 2019

Related U.S. Application Data

(63) Continuation of application No. 14/995,503, filed on Jan. 14, 2016, now abandoned, which is a
(Continued)

(51) Int. Cl.
*A61B 17/70* (2006.01)
*A61F 5/02* (2006.01)
(Continued)

(52) U.S. Cl.
CPC ...... *A61B 17/7074* (2013.01); *A61B 17/7216* (2013.01); *A61F 5/02* (2013.01);
(Continued)

(58) Field of Classification Search
CPC ........ A61B 17/7016; A61B 2019/2253; A61B 17/64–66
See application file for complete search history.

(56) References Cited

U.S. PATENT DOCUMENTS

| 1,599,538 A | 9/1926 | Ludger |
| 3,111,945 A | 11/1963 | Von |

(Continued)

FOREIGN PATENT DOCUMENTS

| AU | 20068468 | 3/2001 |
| CN | 101040807 | 9/2007 |

(Continued)

OTHER PUBLICATIONS

US 9,161,784 B2, 10/2015, Buttermann (withdrawn)
(Continued)

*Primary Examiner* — Julianna N Harvey
(74) *Attorney, Agent, or Firm* — NuVasive, Inc.

(57) ABSTRACT

An external adjustment device includes at least one permanent magnet configured for rotation about an axis with a first handle extending linearly at a first end of the device and a second handle at a second end of the device, the second handle extending in a direction substantially off axis to the first handle. The external adjustment device further includes a motor mounted inside the first handle and a first button located in the proximity to one of the first handle or the second handle, the first button configured to be operated by the thumb of a hand that grips the one of the first handle or second handle. The first button is configured to actuate the motor causing the at least one permanent magnet to rotate about the axis in a first direction.

19 Claims, 7 Drawing Sheets

Related U.S. Application Data continuation of application No. 13/172,598, filed on Jun. 29, 2011, now Pat. No. 9,248,043.

(60) Provisional application No. 61/360,353, filed on Jun. 30, 2010.

(51) Int. Cl.
*A61B 17/72* (2006.01)
*A61B 17/00* (2006.01)
*A61B 17/68* (2006.01)

(52) U.S. Cl.
CPC .............. *A61B 2017/00411* (2013.01); *A61B 2017/00876* (2013.01); *A61B 2017/681* (2013.01)

(56) References Cited

U.S. PATENT DOCUMENTS

| | | |
|---|---|---|
| 3,372,476 A | 3/1968 | Richard et al. |
| 3,377,576 A | 4/1968 | Edwin et al. |
| 3,527,220 A | 6/1968 | Summers |
| 3,397,928 A | 8/1968 | Galle |
| 3,512,901 A | 5/1970 | Law |
| 3,597,781 A | 8/1971 | Eibes et al. |
| 3,726,279 A | 4/1973 | Barefoot et al. |
| 3,749,098 A | 7/1973 | De Bennetot |
| 3,750,194 A | 8/1973 | Summers |
| 3,810,259 A | 5/1974 | Summers |
| 3,840,018 A | 10/1974 | Heifetz |
| 3,866,510 A | 2/1975 | Eibes et al. |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,118,805 A | 10/1978 | Reimels |
| 4,204,541 A | 5/1980 | Kapitanov |
| 4,222,374 A | 9/1980 | Sampson et al. |
| 4,235,246 A | 11/1980 | Weiss |
| 4,256,094 A | 3/1981 | Kapp et al. |
| 4,286,584 A | 9/1981 | Sampson et al. |
| 4,300,223 A | 11/1981 | Maire |
| 4,357,946 A | 11/1982 | Dutcher et al. |
| 4,386,603 A | 6/1983 | Mayfield |
| 4,395,259 A | 7/1983 | Prestele et al. |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,339 A | 6/1986 | Kuzmak et al. |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,696,288 A | 9/1987 | Kuzmak et al. |
| 4,700,091 A | 10/1987 | Wuthrich |
| 4,747,832 A | 5/1988 | Buffet |
| 4,760,837 A | 8/1988 | Petit |
| 4,854,304 A | 8/1989 | Zielke |
| 4,872,515 A | 10/1989 | Lundell |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 4,978,323 A | 12/1990 | Freedman |
| 4,998,013 A | 3/1991 | Epstein et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,053,047 A | 10/1991 | Yoon |
| 5,064,004 A | 11/1991 | Lundell |
| 5,074,868 A | 12/1991 | Kuzmak |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,152,770 A | 10/1992 | Bengmark et al. |
| 5,156,605 A | 10/1992 | Pursley et al. |
| 5,176,618 A | 1/1993 | Freedman |
| 5,180,380 A | 1/1993 | Pursley et al. |
| 5,222,976 A | 6/1993 | Yoon |
| 5,226,429 A | 7/1993 | Kuzmak |
| 5,261,908 A | 11/1993 | Campbell, Jr. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,360,407 A | 11/1994 | Leonard et al. |
| 5,364,396 A | 11/1994 | Robinson et al. |
| 5,381,943 A | 1/1995 | Allen et al. |
| 5,399,168 A | 3/1995 | Wadsworth, Jr. et al. |
| 5,403,322 A | 4/1995 | Herzenberg et al. |
| 5,429,638 A | 7/1995 | Muschler et al. |
| 5,433,721 A | 7/1995 | Hooven et al. |
| 5,437,266 A | 8/1995 | McPherson et al. |
| 5,449,368 A | 9/1995 | Kuzmak |
| 5,466,261 A | 11/1995 | Richelsoph |
| 5,468,030 A | 11/1995 | Walling |
| 5,480,437 A | 1/1996 | Draenert |
| 5,498,262 A | 3/1996 | Bryan |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,536,296 A | 7/1996 | Ten Eyck et al. |
| 5,549,610 A | 8/1996 | Russell et al. |
| 5,573,496 A | 11/1996 | McPherson et al. |
| 5,575,790 A | 11/1996 | Chen et al. |
| 5,582,616 A | 12/1996 | Bolduc et al. |
| 5,601,224 A | 2/1997 | Bishop et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,628,888 A | 5/1997 | Bakhir et al. |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,676,162 A | 10/1997 | Larson, Jr. et al. |
| 5,693,091 A | 12/1997 | Larson, Jr. et al. |
| 5,700,263 A | 12/1997 | Schendel |
| 5,702,430 A | 12/1997 | Larson, Jr. et al. |
| 5,704,893 A | 1/1998 | Timm |
| 5,704,938 A | 1/1998 | Staehlin et al. |
| 5,704,939 A | 1/1998 | Justin |
| 5,720,746 A | 2/1998 | Soubeiran |
| 5,722,429 A | 3/1998 | Larson, Jr. et al. |
| 5,722,930 A | 3/1998 | Larson, Jr. et al. |
| 5,743,910 A | 4/1998 | Bays et al. |
| 5,758,666 A | 6/1998 | Larson, Jr. et al. |
| 5,762,599 A | 6/1998 | Sohn |
| 5,766,208 A | 6/1998 | McEwan |
| 5,771,903 A | 6/1998 | Jakobsson |
| 5,800,434 A | 9/1998 | Campbell, Jr. |
| 5,810,815 A | 9/1998 | Morales |
| 5,824,008 A | 10/1998 | Bolduc et al. |
| 5,827,286 A | 10/1998 | Incavo et al. |
| 5,829,662 A | 11/1998 | Allen et al. |
| 5,830,221 A | 11/1998 | Stein et al. |

(56) References Cited

U.S. PATENT DOCUMENTS

| | | |
|---|---|---|
| 5,843,129 A | 12/1998 | Larson, Jr. et al. |
| 5,874,796 A | 2/1999 | Petersen |
| 5,879,375 A | 3/1999 | Larson, Jr. et al. |
| 5,902,304 A | 5/1999 | Walker et al. |
| 5,935,127 A | 8/1999 | Border |
| 5,938,669 A | 8/1999 | Klaiber et al. |
| 5,945,762 A | 8/1999 | Chen et al. |
| 5,954,915 A | 9/1999 | Voorhees et al. |
| 5,961,553 A | 10/1999 | Coty et al. |
| 5,964,763 A | 10/1999 | Incavo et al. |
| 5,976,138 A | 11/1999 | Baumgart et al. |
| 5,979,456 A | 11/1999 | Magovern |
| 5,985,110 A | 11/1999 | Bakhir et al. |
| 5,997,490 A | 12/1999 | McLeod et al. |
| 6,009,837 A | 1/2000 | McClasky |
| 6,022,349 A | 2/2000 | McLeod et al. |
| 6,033,412 A | 3/2000 | Losken et al. |
| 6,034,296 A | 3/2000 | Elvin et al. |
| 6,067,991 A | 5/2000 | Forsell |
| 6,074,341 A | 6/2000 | Anderson et al. |
| 6,074,882 A | 6/2000 | Eckardt |
| 6,092,531 A | 7/2000 | Chen et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,210,347 B1 | 4/2001 | Forsell |
| 6,217,847 B1 | 4/2001 | Contag et al. |
| 6,221,074 B1 | 4/2001 | Cole et al. |
| 6,234,299 B1 | 5/2001 | Voorhees et al. |
| 6,234,956 B1 | 5/2001 | He et al. |
| 6,241,730 B1 | 6/2001 | Alby |
| 6,245,075 B1 | 6/2001 | Betz et al. |
| 6,283,156 B1 | 9/2001 | Motley |
| 6,296,643 B1 | 10/2001 | Hopf et al. |
| 6,296,656 B1 | 10/2001 | Bolduc et al. |
| 6,299,613 B1 | 10/2001 | Ogilvie et al. |
| 6,315,784 B1 | 11/2001 | Djurovic |
| 6,319,255 B1 | 11/2001 | Grundei et al. |
| 6,321,106 B1 | 11/2001 | Lemelson |
| 6,325,805 B1 | 12/2001 | Ogilvie et al. |
| 6,327,492 B1 | 12/2001 | Lemelson |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,386,083 B1 | 5/2002 | Hwang |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,417,750 B1 | 7/2002 | Sohn |
| 6,423,061 B1 | 7/2002 | Bryant |
| 6,432,040 B1 | 8/2002 | Meah |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,494,879 B2 | 12/2002 | Lennox et al. |
| 6,499,907 B1 | 12/2002 | Baur |
| 6,500,110 B1 | 12/2002 | Davey et al. |
| 6,503,189 B1 | 1/2003 | Forsell |
| 6,508,820 B1 | 1/2003 | Bales |
| 6,510,345 B1 | 1/2003 | Van Bentem |
| 6,511,490 B2 | 1/2003 | Robert |
| 6,527,701 B1 | 3/2003 | Sayet et al. |
| 6,527,702 B2 | 3/2003 | Whalen et al. |
| 6,536,499 B2 | 3/2003 | Voorhees et al. |
| 6,537,196 B1 | 3/2003 | Creighton, IV et al. |
| 6,547,801 B1 | 4/2003 | Dargent et al. |
| 6,554,831 B1 | 4/2003 | Rivard et al. |
| 6,558,400 B2 | 5/2003 | Deem et al. |
| 6,562,051 B1 | 5/2003 | Bolduc et al. |
| 6,565,573 B1 | 5/2003 | Ferrante et al. |
| 6,565,576 B1 | 5/2003 | Stauch et al. |
| 6,573,706 B2 | 6/2003 | Mendes et al. |
| 6,582,313 B2 | 6/2003 | Perrow |
| 6,583,630 B2 | 6/2003 | Mendes et al. |
| 6,587,719 B1 | 7/2003 | Barrett et al. |
| 6,595,912 B2 | 7/2003 | Lau et al. |
| 6,602,184 B2 | 8/2003 | Lau et al. |
| 6,604,529 B2 | 8/2003 | Kim |
| 6,607,363 B1 | 8/2003 | Domroese |
| 6,609,025 B2 | 8/2003 | Barrett et al. |
| 6,612,978 B2 | 9/2003 | Lau et al. |
| 6,612,979 B2 | 9/2003 | Lau et al. |
| 6,616,669 B2 | 9/2003 | Ogilvie et al. |
| 6,621,956 B2 | 9/2003 | Greenaway et al. |
| 6,626,899 B2 | 9/2003 | Houser et al. |
| 6,626,917 B1 | 9/2003 | Craig |
| 6,627,206 B2 | 9/2003 | Lloyd |
| 6,649,143 B1 | 11/2003 | Contag et al. |
| 6,656,135 B2 | 12/2003 | Zogbi et al. |
| 6,656,194 B1 | 12/2003 | Gannoe et al. |
| 6,657,351 B2 | 12/2003 | Chen et al. |
| 6,667,725 B1 | 12/2003 | Simons et al. |
| 6,669,687 B1 | 12/2003 | Saadat |
| 6,673,079 B1 | 1/2004 | Kane |
| 6,676,674 B1 | 1/2004 | Dudai |
| 6,682,474 B2 | 1/2004 | Lau et al. |
| 6,689,046 B2 | 2/2004 | Sayet et al. |
| 6,702,732 B1 | 3/2004 | Lau et al. |
| 6,702,816 B2 | 3/2004 | Buhler |
| 6,706,042 B2 | 3/2004 | Taylor |
| 6,709,293 B2 | 3/2004 | Mori et al. |
| 6,709,385 B2 | 3/2004 | Forsell |
| 6,730,087 B1 | 5/2004 | Butsch |
| 6,749,556 B2 | 6/2004 | Banik |
| 6,752,754 B1 | 6/2004 | Feng et al. |
| 6,761,503 B2 | 7/2004 | Breese |
| 6,765,330 B2 | 7/2004 | Baur |
| 6,769,499 B2 | 8/2004 | Cargill et al. |
| 6,773,437 B2 | 8/2004 | Ogilvie et al. |
| 6,774,624 B2 | 8/2004 | Anderson et al. |
| 6,789,442 B2 | 9/2004 | Forch |
| 6,796,984 B2 | 9/2004 | Soubeiran |
| 6,802,844 B2 | 10/2004 | Ferree |
| 6,802,847 B1 | 10/2004 | Carson et al. |
| 6,809,434 B1 | 10/2004 | Duncan et al. |
| 6,835,183 B2 | 12/2004 | Lennox et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,864,647 B2 | 3/2005 | Duncan et al. |
| 6,884,248 B2 | 4/2005 | Bolduc et al. |
| 6,890,515 B2 | 5/2005 | Contag et al. |
| 6,908,605 B2 | 6/2005 | Contag et al. |
| 6,915,165 B2 | 7/2005 | Forsell |
| 6,916,462 B2 | 7/2005 | Contag et al. |
| 6,918,838 B2 | 7/2005 | Schwarzler et al. |
| 6,918,910 B2 | 7/2005 | Smith et al. |
| 6,921,360 B2 | 7/2005 | Banik |
| 6,921,400 B2 | 7/2005 | Sohngen |
| 6,923,951 B2 | 8/2005 | Contag et al. |
| 6,926,719 B2 | 8/2005 | Sohngen et al. |

(56) References Cited

U.S. PATENT DOCUMENTS

| | | |
|---|---|---|
| 6,939,533 B2 | 9/2005 | Contag et al. |
| 6,953,429 B2 | 10/2005 | Forsell |
| 6,961,553 B2 | 11/2005 | Zhao et al. |
| 6,971,143 B2 | 12/2005 | Domroese |
| 6,980,921 B2 | 12/2005 | Anderson et al. |
| 6,997,952 B2 | 2/2006 | Furukawa et al. |
| 7,001,327 B2 | 2/2006 | Whalen et al. |
| 7,001,346 B2 | 2/2006 | White |
| 7,008,425 B2 | 3/2006 | Phillips |
| 7,011,621 B2 | 3/2006 | Sayet et al. |
| 7,011,658 B2 | 3/2006 | Young |
| 7,011,682 B2 | 3/2006 | Lashinski et al. |
| 7,018,380 B2 | 3/2006 | Cole |
| 7,029,475 B2 | 4/2006 | Panjabi |
| 7,041,105 B2 | 5/2006 | Michelson |
| 7,060,075 B2 | 6/2006 | Govari et al. |
| 7,060,080 B2 | 6/2006 | Bachmann |
| 7,063,706 B2 | 6/2006 | Wittenstein |
| 7,077,802 B2 | 7/2006 | Lau et al. |
| 7,081,086 B2 | 7/2006 | Lau et al. |
| 7,083,629 B2 | 8/2006 | Weller et al. |
| 7,096,148 B2 | 8/2006 | Anderson et al. |
| 7,097,611 B2 | 8/2006 | Lau et al. |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,115,130 B2 | 10/2006 | Michelson |
| 7,124,493 B2 | 10/2006 | Lau et al. |
| 7,128,707 B2 | 10/2006 | Banik |
| 7,135,022 B2 | 11/2006 | Kosashvili et al. |
| 7,160,312 B2 | 1/2007 | Saadat |
| 7,163,538 B2 | 1/2007 | Altarac et al. |
| 7,172,607 B2 | 2/2007 | Hofle et al. |
| 7,175,589 B2 | 2/2007 | Deem et al. |
| 7,175,660 B2 | 2/2007 | Cartledge et al. |
| 7,186,262 B2 | 3/2007 | Saadat |
| 7,188,627 B2 | 3/2007 | Nelson et al. |
| 7,189,005 B2 | 3/2007 | Ward |
| 7,189,202 B2 | 3/2007 | Lau et al. |
| 7,189,251 B2 | 3/2007 | Kay |
| 7,191,007 B2 | 3/2007 | Desai et al. |
| 7,194,297 B2 | 3/2007 | Talpade et al. |
| 7,195,608 B2 | 3/2007 | Burnett |
| 7,198,774 B2 | 4/2007 | Contag et al. |
| 7,211,094 B2 | 5/2007 | Gannoe et al. |
| 7,216,648 B2 | 5/2007 | Nelson et al. |
| 7,217,284 B2 | 5/2007 | Houser et al. |
| 7,218,232 B2 | 5/2007 | DiSilvestro et al. |
| 7,232,449 B2 | 6/2007 | Sharkawy et al. |
| 7,234,468 B2 | 6/2007 | Johnson et al. |
| 7,234,544 B2 | 6/2007 | Kent |
| 7,238,152 B2 | 7/2007 | Lau et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,255,714 B2 | 8/2007 | Malek |
| 7,255,851 B2 | 8/2007 | Contag et al. |
| 7,276,022 B2 | 10/2007 | Lau et al. |
| 7,282,023 B2 | 10/2007 | Frering |
| 7,285,087 B2 | 10/2007 | Moaddeb et al. |
| 7,288,064 B2 | 10/2007 | Boustani et al. |
| 7,288,099 B2 | 10/2007 | Deem et al. |
| 7,288,101 B2 | 10/2007 | Deem et al. |
| 7,296,577 B2 | 11/2007 | Lashinski et al. |
| 7,297,150 B2 | 11/2007 | Cartledge et al. |
| 7,299,091 B2 | 11/2007 | Barrett et al. |
| 7,302,858 B2 | 12/2007 | Walsh et al. |
| 7,306,614 B2 | 12/2007 | Weller et al. |
| 7,311,690 B2 | 12/2007 | Burnett |
| 7,314,372 B2 | 1/2008 | Belfor et al. |
| 7,314,443 B2 | 1/2008 | Jordan et al. |
| 7,320,706 B2 | 1/2008 | Al-Najjar |
| 7,331,995 B2 | 2/2008 | Eisermann et al. |
| 7,333,013 B2 | 2/2008 | Berger |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,361,192 B2 | 4/2008 | Doty |
| 7,364,542 B2 | 4/2008 | Jambor et al. |
| 7,364,589 B2 | 4/2008 | Eisermann |
| 7,367,340 B2 | 5/2008 | Nelson et al. |
| 7,367,937 B2 | 5/2008 | Jambor et al. |
| 7,367,938 B2 | 5/2008 | Forsell |
| 7,371,244 B2 | 5/2008 | Chatlynne et al. |
| 7,374,557 B2 | 5/2008 | Conlon et al. |
| 7,390,007 B2 | 6/2008 | Helms et al. |
| 7,390,294 B2 | 6/2008 | Hassler, Jr. |
| 7,400,926 B2 | 7/2008 | Forsell |
| 7,402,134 B2 | 7/2008 | Moaddeb et al. |
| 7,402,176 B2 | 7/2008 | Malek |
| 7,410,461 B2 | 8/2008 | Lau et al. |
| 7,416,528 B2 | 8/2008 | Crawford et al. |
| 7,422,566 B2 | 9/2008 | Miethke |
| 7,429,259 B2 | 9/2008 | Cadeddu et al. |
| 7,431,692 B2 | 10/2008 | Zollinger et al. |
| 7,441,559 B2 | 10/2008 | Nelson et al. |
| 7,442,196 B2 | 10/2008 | Fisher et al. |
| 7,445,010 B2 | 11/2008 | Kugler et al. |
| 7,455,690 B2 | 11/2008 | Cartledge et al. |
| 7,458,981 B2 | 12/2008 | Fielding et al. |
| 7,468,060 B2 | 12/2008 | Utley et al. |
| 7,476,195 B2 | 1/2009 | Sayet et al. |
| 7,476,238 B2 | 1/2009 | Panjabi |
| 7,481,224 B2 | 1/2009 | Nelson et al. |
| 7,481,763 B2 | 1/2009 | Hassler, Jr. et al. |
| 7,481,841 B2 | 1/2009 | Hazebrouck et al. |
| 7,485,149 B1 | 2/2009 | White |
| 7,489,495 B2 | 2/2009 | Stevenson |
| 7,494,459 B2 | 2/2009 | Anstadt et al. |
| 7,500,484 B2 | 3/2009 | Nelson et al. |
| 7,503,922 B2 | 3/2009 | Deem et al. |
| 7,503,934 B2 | 3/2009 | Eisermann et al. |
| 7,507,252 B2 | 3/2009 | Lashinski et al. |
| 7,510,559 B2 | 3/2009 | Deem et al. |
| 7,530,981 B2 | 5/2009 | Kutsenko |
| 7,531,002 B2 | 5/2009 | Sutton et al. |
| 7,547,291 B2 | 6/2009 | Lennox et al. |
| 7,553,298 B2 | 6/2009 | Hunt et al. |
| 7,559,951 B2 | 7/2009 | DiSilvestro et al. |
| 7,561,916 B2 | 7/2009 | Hunt et al. |
| 7,562,660 B2 | 7/2009 | Saadat |
| 7,566,297 B2 | 7/2009 | Banik |
| 7,569,057 B2 | 8/2009 | Liu et al. |
| 7,578,821 B2 | 8/2009 | Fisher et al. |
| 7,584,788 B2 | 9/2009 | Baron et al. |
| 7,594,887 B2 | 9/2009 | Moaddeb et al. |
| 7,601,156 B2 | 10/2009 | Robinson |
| 7,601,162 B2 | 10/2009 | Hassler, Jr. et al. |
| 7,601,171 B2 | 10/2009 | Ainsworth et al. |
| 7,611,526 B2 | 11/2009 | Carl et al. |
| 7,615,001 B2 | 11/2009 | Jambor et al. |
| 7,615,068 B2 | 11/2009 | Timm et al. |
| 7,618,435 B2 | 11/2009 | Opolski |
| 7,621,886 B2 | 11/2009 | Burnett |
| 7,635,379 B2 | 12/2009 | Callahan et al. |
| 7,651,483 B2 | 1/2010 | Byrum et al. |
| 7,658,753 B2 | 2/2010 | Carl et al. |
| 7,666,132 B2 | 2/2010 | Forsell |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,691,144 B2 | 4/2010 | Chang et al. |
| 7,695,512 B2 | 4/2010 | Lashinski et al. |
| 7,704,279 B2 | 4/2010 | Moskowitz et al. |
| 7,704,282 B2 | 4/2010 | Disilvestro et al. |
| 7,708,737 B2 | 5/2010 | Kraft et al. |

(56) References Cited

U.S. PATENT DOCUMENTS

| | | |
|---|---|---|
| 7,708,762 B2 | 5/2010 | McCarthy et al. |
| 7,708,765 B2 | 5/2010 | Carl et al. |
| 7,708,779 B2 | 5/2010 | Edie et al. |
| 7,713,287 B2 | 5/2010 | Timm et al. |
| 7,717,959 B2 | 5/2010 | William et al. |
| 7,727,141 B2 | 6/2010 | Hassler, Jr. et al. |
| 7,727,143 B2 | 6/2010 | Birk et al. |
| 7,749,224 B2 | 7/2010 | Cresina et al. |
| 7,753,913 B2 | 7/2010 | Szakelyhidi, Jr. et al. |
| 7,753,915 B1 | 7/2010 | Eksler et al. |
| 7,757,552 B2 | 7/2010 | Bogath et al. |
| 7,762,998 B2 | 7/2010 | Birk et al. |
| 7,763,053 B2 | 7/2010 | Gordon |
| 7,763,080 B2 | 7/2010 | Southworth |
| 7,766,815 B2 | 8/2010 | Ortiz |
| 7,775,099 B2 | 8/2010 | Bogath et al. |
| 7,775,215 B2 | 8/2010 | Hassler, Jr. et al. |
| 7,776,061 B2 | 8/2010 | Garner et al. |
| 7,776,068 B2 | 8/2010 | Ainsworth et al. |
| 7,776,075 B2 | 8/2010 | Bruneau et al. |
| 7,776,091 B2 | 8/2010 | Mastrorio et al. |
| 7,780,590 B2 | 8/2010 | Birk et al. |
| 7,787,958 B2 | 8/2010 | Stevenson |
| 7,789,912 B2 | 9/2010 | Manzi et al. |
| 7,793,583 B2 | 9/2010 | Radinger et al. |
| 7,794,447 B2 | 9/2010 | Dann et al. |
| 7,794,476 B2 | 9/2010 | Wisnewski |
| 7,798,954 B2 | 9/2010 | Birk et al. |
| 7,799,080 B2 | 9/2010 | Doty |
| 7,803,106 B2 | 9/2010 | Whalen et al. |
| 7,803,157 B2 | 9/2010 | Michelson |
| 7,811,275 B2 | 10/2010 | Birk et al. |
| 7,811,298 B2 | 10/2010 | Birk |
| 7,811,328 B2 | 10/2010 | Molz, IV et al. |
| 7,815,643 B2 | 10/2010 | Johnson et al. |
| 7,828,714 B2 | 11/2010 | Feng et al. |
| 7,828,813 B2 | 11/2010 | Mouton |
| 7,833,228 B1 | 11/2010 | Hershberger |
| 7,835,779 B2 | 11/2010 | Anderson et al. |
| 7,837,669 B2 | 11/2010 | Dann et al. |
| 7,837,691 B2 | 11/2010 | Cordes et al. |
| 7,842,036 B2 | 11/2010 | Phillips |
| 7,845,356 B2 | 12/2010 | Paraschac et al. |
| 7,846,188 B2 | 12/2010 | Moskowitz et al. |
| 7,850,660 B2 | 12/2010 | Uth et al. |
| 7,850,735 B2 | 12/2010 | Eisermann et al. |
| 7,854,769 B2 | 12/2010 | Hershberger |
| 7,862,546 B2 | 1/2011 | Conlon et al. |
| 7,862,574 B2 | 1/2011 | Deem et al. |
| 7,862,586 B2 | 1/2011 | Malek |
| 7,867,235 B2 | 1/2011 | Fell et al. |
| 7,871,368 B2 | 1/2011 | Zollinger et al. |
| 7,875,033 B2 | 1/2011 | Richter et al. |
| 7,887,566 B2 | 2/2011 | Hynes |
| 7,901,381 B2 | 3/2011 | Birk et al. |
| 7,901,419 B2 | 3/2011 | Bachmann et al. |
| 7,909,790 B2 | 3/2011 | Burnett |
| 7,909,838 B2 | 3/2011 | Deem et al. |
| 7,909,839 B2 | 3/2011 | Fields |
| 7,909,852 B2 | 3/2011 | Boomer et al. |
| 7,918,844 B2 | 4/2011 | Byrum et al. |
| 7,921,850 B2 | 4/2011 | Nelson et al. |
| 7,922,765 B2 | 4/2011 | Reiley |
| 7,927,354 B2 | 4/2011 | Edidin et al. |
| 7,927,357 B2 | 4/2011 | Sacher et al. |
| 7,931,679 B2 | 4/2011 | Heggeness |
| 7,932,825 B2 | 4/2011 | Berger |
| 7,938,836 B2 | 5/2011 | Ainsworth et al. |
| 7,938,841 B2 | 5/2011 | Sharkawy et al. |
| 7,942,903 B2 | 5/2011 | Moskowitz et al. |
| 7,942,908 B2 | 5/2011 | Sacher et al. |
| 7,947,011 B2 | 5/2011 | Birk et al. |
| 7,951,067 B2 | 5/2011 | Byrum et al. |
| 7,951,180 B2 | 5/2011 | Moskowitz et al. |
| 7,958,895 B2 | 6/2011 | Nelson et al. |
| 7,958,896 B2 | 6/2011 | Nelson et al. |
| 7,959,552 B2 | 6/2011 | Jordan et al. |
| 7,972,315 B2 | 7/2011 | Birk et al. |
| 7,972,346 B2 | 7/2011 | Bachmann et al. |
| 7,972,363 B2 | 7/2011 | Moskowitz et al. |
| 7,976,545 B2 | 7/2011 | Hershberger et al. |
| 7,983,763 B2 | 7/2011 | Stevenson et al. |
| 7,985,256 B2 | 7/2011 | Grotz et al. |
| 7,987,241 B2 | 7/2011 | St Jacques, Jr. et al. |
| 7,988,707 B2 | 8/2011 | Panjabi |
| 7,988,709 B2 | 8/2011 | Clark et al. |
| 7,993,342 B2 | 8/2011 | Malandain et al. |
| 7,993,397 B2 | 8/2011 | Lashinski et al. |
| 7,998,174 B2 | 8/2011 | Malandain et al. |
| 7,998,208 B2 | 8/2011 | Kohm et al. |
| 8,002,801 B2 | 8/2011 | Carl et al. |
| 8,002,809 B2 | 8/2011 | Baynham |
| 8,007,458 B2 | 8/2011 | Lennox et al. |
| 8,007,474 B2 | 8/2011 | Uth et al. |
| 8,007,479 B2 | 8/2011 | Birk et al. |
| 8,011,308 B2 | 9/2011 | Picchio |
| 8,012,162 B2 | 9/2011 | Bachmann |
| 8,016,745 B2 | 9/2011 | Hassler, Jr. et al. |
| 8,016,837 B2 | 9/2011 | Giger et al. |
| 8,016,860 B2 | 9/2011 | Carl et al. |
| 8,026,729 B2 | 9/2011 | Kroh et al. |
| 8,029,477 B2 | 10/2011 | Byrum et al. |
| 8,029,567 B2 | 10/2011 | Edidin et al. |
| 8,034,080 B2 | 10/2011 | Malandain et al. |
| 8,037,871 B2 | 10/2011 | McClendon |
| 8,038,680 B2 | 10/2011 | Ainsworth et al. |
| 8,038,698 B2 | 10/2011 | Edidin et al. |
| 8,043,206 B2 | 10/2011 | Birk |
| 8,043,290 B2 | 10/2011 | Harrison et al. |
| 8,043,299 B2 | 10/2011 | Conway |
| 8,043,338 B2 | 10/2011 | Dant |
| 8,043,345 B2 | 10/2011 | Carl et al. |
| 8,048,169 B2 | 11/2011 | Burnett et al. |
| 8,057,473 B2 | 11/2011 | Orsak et al. |
| 8,057,513 B2 | 11/2011 | Kohm et al. |
| 8,066,650 B2 | 11/2011 | Lee et al. |
| 8,070,670 B2 | 12/2011 | Deem et al. |
| 8,070,671 B2 | 12/2011 | Deem et al. |
| 8,070,695 B2 | 12/2011 | Gupta et al. |
| 8,070,813 B2 | 12/2011 | Grotz et al. |
| 8,074,654 B2 | 12/2011 | Paraschac et al. |
| 8,075,577 B2 | 12/2011 | Deem et al. |
| 8,079,974 B2 | 12/2011 | Stergiopulos |
| 8,079,989 B2 | 12/2011 | Birk et al. |
| 8,080,022 B2 | 12/2011 | Deem et al. |
| 8,080,025 B2 | 12/2011 | Deem et al. |
| 8,088,166 B2 | 1/2012 | Makower et al. |
| 8,092,459 B2 | 1/2012 | Malandain |
| 8,092,499 B1 | 1/2012 | Roth |
| 8,095,317 B2 | 1/2012 | Ekseth et al. |
| 8,096,302 B2 | 1/2012 | Nelson et al. |
| 8,096,938 B2 | 1/2012 | Forsell |
| 8,096,995 B2 | 1/2012 | Kohm et al. |
| 8,097,018 B2 | 1/2012 | Malandain et al. |
| 8,097,038 B2 | 1/2012 | Malek |
| 8,100,819 B2 | 1/2012 | Banik |
| 8,100,943 B2 | 1/2012 | Malandain et al. |
| 8,100,967 B2 | 1/2012 | Makower et al. |
| 8,105,360 B1 | 1/2012 | Connor |
| 8,105,363 B2 | 1/2012 | Fielding et al. |
| 8,105,364 B2 | 1/2012 | McCarthy et al. |
| 8,109,974 B2 | 2/2012 | Boomer et al. |
| 8,114,158 B2 | 2/2012 | Carl et al. |
| 8,123,765 B2 | 2/2012 | Deem et al. |
| 8,123,805 B2 | 2/2012 | Makower et al. |
| 8,128,628 B2 | 3/2012 | Freid et al. |
| 8,133,280 B2 | 3/2012 | Voellmicke et al. |
| 8,137,349 B2 | 3/2012 | Soubeiran |
| 8,137,366 B2 | 3/2012 | Deem et al. |
| 8,137,367 B2 | 3/2012 | Deem et al. |
| 8,142,454 B2 | 3/2012 | Harrison et al. |
| 8,142,494 B2 | 3/2012 | Randert et al. |
| 8,147,517 B2 | 4/2012 | Trieu et al. |
| 8,147,549 B2 | 4/2012 | Metcalf, Jr. et al. |

(56) References Cited

U.S. PATENT DOCUMENTS

| | | |
|---|---|---|
| 8,157,841 B2 | 4/2012 | Malandain et al. |
| 8,162,897 B2 | 4/2012 | Byrum |
| 8,162,979 B2 | 4/2012 | Sachs et al. |
| 8,163,013 B2 | 4/2012 | Machold et al. |
| 8,177,789 B2 | 5/2012 | Magill et al. |
| 8,182,411 B2 | 5/2012 | Dlugos |
| 8,187,324 B2 | 5/2012 | Webler et al. |
| 8,197,544 B1 | 6/2012 | Manzi et al. |
| 8,202,305 B2 | 6/2012 | Reiley |
| 8,211,127 B2 | 7/2012 | Uth et al. |
| 8,211,149 B2 | 7/2012 | Justis |
| 8,211,151 B2 | 7/2012 | Schwab et al. |
| 8,211,179 B2 | 7/2012 | Molz, IV et al. |
| 8,216,275 B2 | 7/2012 | Fielding et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,292 B2 | 8/2012 | Collazo |
| 8,241,293 B2 | 8/2012 | Stone et al. |
| 8,241,331 B2 | 8/2012 | Arnin |
| 8,246,630 B2 | 8/2012 | Manzi et al. |
| 8,251,888 B2 | 8/2012 | Roslin et al. |
| 8,252,063 B2 | 8/2012 | Stauch |
| 8,257,370 B2 | 9/2012 | Moskowitz et al. |
| 8,257,442 B2 | 9/2012 | Edie et al. |
| 8,263,024 B2 | 9/2012 | Wan et al. |
| 8,267,969 B2 | 9/2012 | Altarac et al. |
| 8,273,112 B2 | 9/2012 | Garamszegi et al. |
| 8,278,941 B2 | 10/2012 | Kroh et al. |
| 8,282,671 B2 | 10/2012 | Connor |
| 8,287,540 B2 | 10/2012 | LeCronier et al. |
| 8,298,133 B2 | 10/2012 | Wiley et al. |
| 8,298,240 B2 | 10/2012 | Giger et al. |
| 8,308,779 B2 | 11/2012 | Reiley |
| 8,313,423 B2 | 11/2012 | Forsell |
| 8,316,856 B2 | 11/2012 | Nelson et al. |
| 8,317,761 B2 | 11/2012 | Birk et al. |
| 8,317,802 B1 | 11/2012 | Manzi et al. |
| 8,323,290 B2 | 12/2012 | Metzger et al. |
| 8,326,435 B2 | 12/2012 | Stevenson |
| 8,328,807 B2 | 12/2012 | Brigido |
| 8,328,854 B2 | 12/2012 | Baynham et al. |
| 8,333,204 B2 | 12/2012 | Saadat |
| 8,333,790 B2 | 12/2012 | Timm et al. |
| 8,353,913 B2 | 1/2013 | Moskowitz et al. |
| 8,357,169 B2 | 1/2013 | Henniges et al. |
| 8,357,182 B2 | 1/2013 | Seme |
| 8,357,183 B2 | 1/2013 | Seme et al. |
| 8,360,955 B2 | 1/2013 | Sayet et al. |
| 8,366,628 B2 | 2/2013 | Denker et al. |
| 8,372,078 B2 | 2/2013 | Collazo |
| 8,382,652 B2 | 2/2013 | Sayet et al. |
| 8,386,018 B2 | 2/2013 | Stauch et al. |
| 8,388,667 B2 | 3/2013 | Reiley et al. |
| 8,394,124 B2 | 3/2013 | Biyani |
| 8,394,143 B2 | 3/2013 | Grotz et al. |
| 8,403,958 B2 | 3/2013 | Schwab |
| 8,409,203 B2 | 4/2013 | Birk et al. |
| 8,409,281 B2 | 4/2013 | Makower et al. |
| 8,414,584 B2 | 4/2013 | Brigido |
| 8,414,648 B2 | 4/2013 | Reiley |
| 8,419,755 B2 | 4/2013 | Deem et al. |
| 8,419,801 B2 | 4/2013 | DiSilvestro et al. |
| 8,425,570 B2 | 4/2013 | Reiley |
| 8,425,608 B2 | 4/2013 | Dewey et al. |
| 8,433,519 B2 | 4/2013 | Ekseth et al. |
| 8,435,268 B2 | 5/2013 | Thompson et al. |
| 8,439,915 B2 | 5/2013 | Harrison et al. |
| 8,439,926 B2 | 5/2013 | Bojarski et al. |
| 8,444,693 B2 | 5/2013 | Reiley |
| 8,449,553 B2 | 5/2013 | Kam et al. |
| 8,449,580 B2 | 5/2013 | Voellmicke et al. |
| 8,454,695 B2 | 6/2013 | Grotz et al. |
| 8,469,908 B2 | 6/2013 | Asfora |
| 8,469,978 B2 | 6/2013 | Fobi et al. |
| 8,470,003 B2 | 6/2013 | Voellmicke et al. |
| 8,470,004 B2 | 6/2013 | Reiley |
| 8,475,354 B2 | 7/2013 | Phillips et al. |
| 8,475,356 B2 | 7/2013 | Feng et al. |
| 8,475,499 B2 | 7/2013 | Cournoyer et al. |
| 8,480,554 B2 | 7/2013 | Phillips et al. |
| 8,480,668 B2 | 7/2013 | Fernandez et al. |
| 8,480,741 B2 | 7/2013 | Grotz et al. |
| 8,486,070 B2 | 7/2013 | Morgan et al. |
| 8,486,076 B2 | 7/2013 | Chavarria et al. |
| 8,486,110 B2 | 7/2013 | Fielding et al. |
| 8,486,113 B2 | 7/2013 | Malek |
| 8,486,147 B2 | 7/2013 | de Villiers et al. |
| 8,491,589 B2 | 7/2013 | Fisher et al. |
| 8,494,805 B2 | 7/2013 | Roche et al. |
| 8,496,662 B2 | 7/2013 | Novak et al. |
| 8,500,810 B2 | 8/2013 | Mastrorio et al. |
| 8,506,517 B2 | 8/2013 | Stergiopulos |
| 8,506,569 B2 | 8/2013 | Keefer et al. |
| 8,517,973 B2 | 8/2013 | Burnett |
| 8,518,062 B2 | 8/2013 | Cole et al. |
| 8,518,086 B2 | 8/2013 | Seme et al. |
| 8,522,790 B2 | 9/2013 | Nelson et al. |
| 8,523,865 B2 | 9/2013 | Reglos et al. |
| 8,523,866 B2 | 9/2013 | Sidebotham et al. |
| 8,523,883 B2 | 9/2013 | Saadat |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,529,630 B2 | 9/2013 | Bojarski et al. |
| 8,545,384 B2 | 10/2013 | Forsell |
| 8,545,508 B2 | 10/2013 | Collazo |
| 8,545,814 B2 | 10/2013 | Contag et al. |
| 8,551,092 B2 | 10/2013 | Morgan et al. |
| 8,551,142 B2 | 10/2013 | Altarac et al. |
| 8,551,422 B2 | 10/2013 | Wan et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,416 B2 | 10/2013 | Schmitz et al. |
| 8,568,457 B2 | 10/2013 | Hunziker |
| 8,574,267 B2 | 11/2013 | Linares |
| 8,579,919 B2 | 11/2013 | Bolduc et al. |
| 8,579,979 B2 | 11/2013 | Edie et al. |
| 8,585,595 B2 | 11/2013 | Heilman |
| 8,585,702 B2 | 11/2013 | Orsak et al. |
| 8,585,738 B2 | 11/2013 | Linares |
| 8,585,740 B1 | 11/2013 | Ross et al. |
| 8,591,549 B2 | 11/2013 | Lange |
| 8,597,362 B2 | 12/2013 | Shenoy et al. |
| 8,613,749 B2 | 12/2013 | Deem et al. |
| 8,613,758 B2 | 12/2013 | Linares |
| 8,617,212 B2 | 12/2013 | Linares |
| 8,617,220 B2 | 12/2013 | Skaggs |
| 8,617,243 B2 | 12/2013 | Eisermann et al. |
| 8,622,936 B2 | 1/2014 | Schenberger et al. |
| 8,623,036 B2 | 1/2014 | Harrison et al. |
| 8,623,042 B2 | 1/2014 | Roslin et al. |
| 8,623,056 B2 | 1/2014 | Linares |
| 8,632,544 B2 | 1/2014 | Haaja et al. |
| 8,632,547 B2 | 1/2014 | Maxson et al. |
| 8,632,548 B2 | 1/2014 | Soubeiran |
| 8,632,563 B2 | 1/2014 | Nagase et al. |
| 8,632,594 B2 | 1/2014 | Williams et al. |
| 8,636,770 B2 | 1/2014 | Hestad et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,652,175 B2 | 2/2014 | Timm et al. |
| 8,657,765 B2 | 2/2014 | Asfora |
| 8,657,856 B2 | 2/2014 | Gephart et al. |
| 8,657,885 B2 | 2/2014 | Burnett et al. |
| 8,663,139 B2 | 3/2014 | Asfora |
| 8,663,140 B2 | 3/2014 | Asfora |
| 8,663,285 B2 | 3/2014 | Dall et al. |
| 8,663,287 B2 | 3/2014 | Butler et al. |
| 8,663,338 B2 | 3/2014 | Burnett et al. |

(56) References Cited

U.S. PATENT DOCUMENTS

| | | |
|---|---|---|
| 8,668,719 B2 | 3/2014 | Alamin et al. |
| 8,673,001 B2 | 3/2014 | Cartledge et al. |
| 8,679,161 B2 | 3/2014 | Malandain et al. |
| 8,690,858 B2 | 4/2014 | Machold et al. |
| 8,707,959 B2 | 4/2014 | Paraschac et al. |
| 8,709,090 B2 | 4/2014 | Makower et al. |
| 8,715,243 B2 | 5/2014 | Uth et al. |
| 8,715,290 B2 | 5/2014 | Fisher et al. |
| 8,721,570 B2 | 5/2014 | Gupta et al. |
| 8,721,643 B2 | 5/2014 | Morgan et al. |
| 8,728,125 B2 | 5/2014 | Bruneau et al. |
| 8,734,318 B2 | 5/2014 | Forsell |
| 8,734,516 B2 | 5/2014 | Moskowitz et al. |
| 8,734,519 B2 | 5/2014 | de Villiers et al. |
| 8,747,444 B2 | 6/2014 | Moskowitz et al. |
| 8,752,552 B2 | 6/2014 | Nelson et al. |
| 8,758,303 B2 | 6/2014 | Uth et al. |
| 8,758,347 B2 | 6/2014 | Weiner et al. |
| 8,758,355 B2 | 6/2014 | Fisher et al. |
| 8,758,372 B2 | 6/2014 | Cartledge et al. |
| 8,762,308 B2 | 6/2014 | Najarian et al. |
| 8,764,713 B2 | 7/2014 | Uth et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,781,744 B2 | 7/2014 | Ekseth et al. |
| 8,784,482 B2 | 7/2014 | Rahdert et al. |
| 8,790,343 B2 | 7/2014 | McClellan et al. |
| 8,790,380 B2 | 7/2014 | Buttermann |
| 8,790,409 B2 | 7/2014 | Van den Heuvel et al. |
| 8,794,243 B2 | 8/2014 | Deem et al. |
| 8,795,339 B2 | 8/2014 | Boomer et al. |
| 8,801,795 B2 | 8/2014 | Makower et al. |
| 8,808,206 B2 | 8/2014 | Asfora |
| 8,813,727 B2 | 8/2014 | McClendon |
| 8,814,869 B2 | 8/2014 | Freid et al. |
| 8,828,058 B2 | 9/2014 | Elsebaie et al. |
| 8,828,087 B2 | 9/2014 | Stone et al. |
| 8,840,623 B2 | 9/2014 | Reiley |
| 8,840,651 B2 | 9/2014 | Reiley |
| 8,845,692 B2 | 9/2014 | Wisnewski |
| 8,845,724 B2 | 9/2014 | Shenoy et al. |
| 8,864,717 B2 | 10/2014 | Conlon et al. |
| 8,864,823 B2 | 10/2014 | Cartledge et al. |
| 8,870,881 B2 | 10/2014 | Rezach et al. |
| 8,870,918 B2 | 10/2014 | Boomer et al. |
| 8,870,959 B2 | 10/2014 | Arnin |
| 8,882,699 B2 | 11/2014 | Burnett |
| 8,882,830 B2 | 11/2014 | Cartledge et al. |
| 8,888,672 B2 | 11/2014 | Phillips et al. |
| 8,888,673 B2 | 11/2014 | Phillips et al. |
| 8,894,663 B2 | 11/2014 | Giger et al. |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,932,247 B2 | 1/2015 | Stergiopulos |
| 8,945,188 B2 | 2/2015 | Rezach et al. |
| 8,945,210 B2 | 2/2015 | Cartledge et al. |
| 8,956,407 B2 | 2/2015 | Macoviak et al. |
| 8,961,386 B2 | 2/2015 | Phillips et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,968,406 B2 | 3/2015 | Arnin |
| 8,986,348 B2 | 3/2015 | Reiley |
| 8,992,527 B2 | 3/2015 | Guichet |
| 9,005,251 B2 | 4/2015 | Heggeness |
| 9,005,293 B2 | 4/2015 | Moskowitz et al. |
| 9,005,298 B2 | 4/2015 | Makower et al. |
| 9,011,491 B2 | 4/2015 | Carl et al. |
| 9,015,057 B2 | 4/2015 | Phillips et al. |
| 9,022,917 B2 | 5/2015 | Kasic et al. |
| 9,028,550 B2 | 5/2015 | Shulock et al. |
| 9,033,957 B2 | 5/2015 | Cadeddu et al. |
| 9,033,988 B2 | 5/2015 | Gephart et al. |
| 9,034,016 B2 | 5/2015 | Panjabi |
| 9,044,218 B2 | 6/2015 | Young |
| 9,060,810 B2 | 6/2015 | Kercher et al. |
| 9,060,844 B2 | 6/2015 | Kagan et al. |
| 9,072,530 B2 | 7/2015 | Mehta et al. |
| 9,072,606 B2 | 7/2015 | Lucas et al. |
| 9,078,703 B2 | 7/2015 | Arnin |
| 9,084,632 B2 | 7/2015 | Orsak et al. |
| 9,089,348 B2 | 7/2015 | Chavarria et al. |
| 9,095,436 B2 | 8/2015 | Boyden et al. |
| 9,095,437 B2 | 8/2015 | Boyden et al. |
| 9,101,422 B2 | 8/2015 | Freid et al. |
| 9,101,427 B2 | 8/2015 | Globerman et al. |
| 9,107,706 B2 | 8/2015 | Alamin et al. |
| 9,113,967 B2 | 8/2015 | Soubeiran |
| 9,114,016 B2 | 8/2015 | Shenoy et al. |
| 9,125,746 B2 | 9/2015 | Clifford et al. |
| 9,138,266 B2 | 9/2015 | Stauch |
| 9,144,482 B2 | 9/2015 | Sayet |
| 9,155,565 B2 | 10/2015 | Boomer et al. |
| 9,161,856 B2 | 10/2015 | Nelson et al. |
| 9,168,071 B2 | 10/2015 | Seme et al. |
| 9,168,076 B2 | 10/2015 | Patty et al. |
| 9,173,681 B2 | 11/2015 | Seme |
| 9,173,715 B2 | 11/2015 | Baumgartner |
| 9,186,158 B2 | 11/2015 | Anthony et al. |
| 9,186,185 B2 | 11/2015 | Hestad et al. |
| 9,198,771 B2 | 12/2015 | Ciupik |
| 9,204,899 B2 | 12/2015 | Buttermann |
| 9,204,908 B2 | 12/2015 | Buttermann |
| 9,220,536 B2 | 12/2015 | Skaggs |
| 9,226,783 B2 | 1/2016 | Brigido |
| 9,242,070 B2 | 1/2016 | Tieu |
| 9,259,243 B2 | 2/2016 | Giger et al. |
| 9,272,159 B2 | 3/2016 | Phillips et al. |
| 9,278,004 B2 | 3/2016 | Shenoy et al. |
| 9,278,046 B2 | 3/2016 | Asfora |
| 9,282,997 B2 | 3/2016 | Hunziker |
| 9,301,792 B2 | 4/2016 | Henniges et al. |
| 9,301,854 B2 | 4/2016 | Moskowitz et al. |
| 9,308,089 B2 | 4/2016 | Vicatos et al. |
| 9,308,387 B2 | 4/2016 | Phillips et al. |
| 9,320,618 B2 | 4/2016 | Schmitz et al. |
| 9,326,728 B2 | 5/2016 | Demir et al. |
| 9,333,009 B2 | 5/2016 | Kroll et al. |
| 9,339,197 B2 | 5/2016 | Griswold et al. |
| 9,339,300 B2 | 5/2016 | Kantelhardt |
| 9,339,307 B2 | 5/2016 | McClintock et al. |
| 9,339,312 B2 | 5/2016 | Doherty et al. |
| 9,358,044 B2 | 6/2016 | Seme et al. |
| 9,364,267 B2 | 6/2016 | Northcutt et al. |
| 9,370,388 B2 | 6/2016 | Globerman et al. |
| 9,393,123 B2 | 7/2016 | Lucas et al. |
| 9,408,644 B2 | 8/2016 | Zahrly et al. |
| 9,421,347 B2 | 8/2016 | Burnett |
| 9,427,267 B2 | 8/2016 | Homeier et al. |
| 9,439,744 B2 | 9/2016 | Forsell |
| 9,439,797 B2 | 9/2016 | Baym et al. |
| 9,445,848 B2 | 9/2016 | Anderson et al. |
| 9,451,997 B2 | 9/2016 | Carl et al. |
| 9,456,953 B2 | 10/2016 | Asfora |
| 9,474,612 B2 | 10/2016 | Haaja et al. |
| 9,492,199 B2 | 11/2016 | Orsak et al. |
| 9,492,276 B2 | 11/2016 | Lee et al. |
| 9,498,258 B2 | 11/2016 | Boomer et al. |
| 9,498,366 B2 | 11/2016 | Burnett et al. |
| 9,510,834 B2 | 12/2016 | Burnett et al. |
| 9,532,804 B2 | 1/2017 | Clifford et al. |
| 9,561,062 B2 | 2/2017 | Hayes et al. |
| 9,561,063 B2 | 2/2017 | Reiley |
| 9,572,588 B2 | 2/2017 | Fisher et al. |
| 9,572,746 B2 | 2/2017 | Asfora |
| 9,572,910 B2 | 2/2017 | Messersmith et al. |
| 9,579,110 B2 | 2/2017 | Bojarski et al. |
| 9,579,203 B2 | 2/2017 | Soubeiran |
| 9,603,605 B2 | 3/2017 | Collazo |
| 9,603,713 B2 | 3/2017 | Moskowitz et al. |
| 9,610,161 B2 | 4/2017 | Macoviak et al. |
| 9,622,875 B2 | 4/2017 | Moskowitz et al. |

(56) References Cited

U.S. PATENT DOCUMENTS

| | | |
|---|---|---|
| 9,642,735 B2 | 5/2017 | Burnett |
| 9,655,651 B2 | 5/2017 | Panjabi |
| 9,668,868 B2 | 6/2017 | Shenoy et al. |
| 9,687,243 B2 | 6/2017 | Burnett et al. |
| 9,687,414 B2 | 6/2017 | Asfora |
| 9,693,867 B2 | 7/2017 | Lucas et al. |
| 9,700,419 B2 | 7/2017 | Clifford et al. |
| 9,700,450 B2 | 7/2017 | Burnett |
| 9,717,537 B2 | 8/2017 | Gordon |
| 9,724,135 B2 | 8/2017 | Koch et al. |
| 9,724,265 B2 | 8/2017 | Asfora |
| 9,730,738 B2 | 8/2017 | Gephart et al. |
| 9,743,969 B2 | 8/2017 | Reiley |
| 9,782,206 B2 | 10/2017 | Mueckter et al. |
| 9,795,410 B2 | 10/2017 | Shenoy et al. |
| 9,814,600 B2 | 11/2017 | Shulock et al. |
| 9,820,789 B2 | 11/2017 | Reiley |
| 9,826,987 B2 | 11/2017 | Keefer et al. |
| 9,833,291 B2 | 12/2017 | Baumgartner |
| 9,848,894 B2 | 12/2017 | Burley et al. |
| 9,848,993 B2 | 12/2017 | Moskowitz et al. |
| 9,861,376 B2 | 1/2018 | Chavarria et al. |
| 9,861,390 B2 | 1/2018 | Hunziker |
| 9,861,404 B2 | 1/2018 | Reiley |
| 9,867,719 B2 | 1/2018 | Moskowitz et al. |
| 2001/0011543 A1 | 8/2001 | Forsell |
| 2002/0019580 A1 | 2/2002 | Lau et al. |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0019498 A1 | 1/2003 | Forsell |
| 2003/0040671 A1 | 2/2003 | Somogyi et al. |
| 2003/0066536 A1 | 4/2003 | Forsell |
| 2003/0114731 A1 | 6/2003 | Cadeddu et al. |
| 2003/0187447 A1 | 10/2003 | Ferrante et al. |
| 2003/0208212 A1 | 11/2003 | Cigaina |
| 2003/0220643 A1 | 11/2003 | Ferree |
| 2003/0220644 A1 | 11/2003 | Thelen et al. |
| 2004/0006342 A1 | 1/2004 | Altarac et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0064030 A1 | 4/2004 | Forsell |
| 2004/0068205 A1 | 4/2004 | Zogbi et al. |
| 2004/0092939 A1 | 5/2004 | Freid et al. |
| 2004/0098121 A1 | 5/2004 | Opolski |
| 2004/0116773 A1 | 6/2004 | Furness et al. |
| 2004/0133219 A1 | 7/2004 | Forsell |
| 2004/0138725 A1 | 7/2004 | Forsell |
| 2004/0153106 A1 | 8/2004 | Dudai |
| 2004/0158254 A1 | 8/2004 | Eisermann |
| 2004/0172040 A1 | 9/2004 | Heggeness |
| 2004/0173222 A1 | 9/2004 | Kim |
| 2004/0193266 A1 | 9/2004 | Meyer |
| 2004/0220567 A1 | 11/2004 | Eisermann et al. |
| 2004/0220668 A1 | 11/2004 | Eisermann et al. |
| 2004/0230307 A1 | 11/2004 | Eisermann |
| 2004/0250820 A1 | 12/2004 | Forsell |
| 2004/0260287 A1 | 12/2004 | Ferree |
| 2004/0260319 A1 | 12/2004 | Egle |
| 2005/0002984 A1 | 1/2005 | Byrum et al. |
| 2005/0043802 A1 | 2/2005 | Eisermann et al. |
| 2005/0055025 A1 | 3/2005 | Zacouto et al. |
| 2005/0070937 A1 | 3/2005 | Jambor et al. |
| 2005/0080427 A1 | 4/2005 | Govari et al. |
| 2005/0080439 A1 | 4/2005 | Carson et al. |
| 2005/0090823 A1 | 4/2005 | Bartimus |
| 2005/0096750 A1 | 5/2005 | Kagan et al. |
| 2005/0131352 A1 | 6/2005 | Conlon et al. |
| 2005/0159754 A1 | 7/2005 | Odrich |
| 2005/0159755 A1 | 7/2005 | Odrich |
| 2005/0165440 A1 | 7/2005 | Cancel et al. |
| 2005/0171543 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182412 A1 | 8/2005 | Johnson et al. |
| 2005/0192629 A1 | 9/2005 | Saadat et al. |
| 2005/0222489 A1 | 10/2005 | Rahdert et al. |
| 2005/0234289 A1 | 10/2005 | Anstadt et al. |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka et al. |
| 2005/0288672 A1 | 12/2005 | Ferree |
| 2006/0020278 A1 | 1/2006 | Burnett et al. |
| 2006/0036251 A1 | 2/2006 | Reiley |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0079897 A1 | 4/2006 | Harrison et al. |
| 2006/0116757 A1 | 6/2006 | Lashinski et al. |
| 2006/0124140 A1 | 6/2006 | Forsell |
| 2006/0136062 A1 | 6/2006 | DiNello et al. |
| 2006/0142634 A1 | 6/2006 | Anstadt et al. |
| 2006/0142767 A1 | 6/2006 | Green et al. |
| 2006/0155279 A1 | 7/2006 | Ogilvie |
| 2006/0155347 A1 | 7/2006 | Forsell |
| 2006/0184240 A1 | 8/2006 | Jimenez et al. |
| 2006/0184248 A1 | 8/2006 | Edidin et al. |
| 2006/0195102 A1 | 8/2006 | Malandain |
| 2006/0204156 A1 | 9/2006 | Takehara et al. |
| 2006/0211909 A1 | 9/2006 | Anstadt et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0249914 A1 | 11/2006 | Dulin |
| 2006/0252983 A1 | 11/2006 | Lembo et al. |
| 2006/0271107 A1 | 11/2006 | Harrison et al. |
| 2006/0276812 A1 | 12/2006 | Hill et al. |
| 2006/0282073 A1 | 12/2006 | Simanovsky |
| 2006/0289014 A1 | 12/2006 | Purdy et al. |
| 2006/0293671 A1 | 12/2006 | Heggeness |
| 2006/0293683 A1 | 12/2006 | Stauch |
| 2007/0010814 A1 | 1/2007 | Stauch |
| 2007/0015955 A1 | 1/2007 | Tsonton |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0055237 A1 | 3/2007 | Edidin et al. |
| 2007/0055368 A1 | 3/2007 | Rhee et al. |
| 2007/0118215 A1 | 5/2007 | Moaddeb |
| 2007/0135913 A1 | 6/2007 | Moaddeb et al. |
| 2007/0162032 A1 | 7/2007 | Johnson et al. |
| 2007/0173837 A1 | 7/2007 | Chan et al. |
| 2007/0173869 A1 | 7/2007 | Gannoe et al. |
| 2007/0179493 A1 | 8/2007 | Kim |
| 2007/0213751 A1 | 9/2007 | Scirica et al. |
| 2007/0239159 A1 | 10/2007 | Altarac et al. |
| 2007/0250084 A1 | 10/2007 | Sharkawy et al. |
| 2007/0255088 A1 | 11/2007 | Jacobson et al. |
| 2007/0256693 A1 | 11/2007 | Paraschac et al. |
| 2007/0260270 A1 | 11/2007 | Assell et al. |
| 2007/0264605 A1 | 11/2007 | Belfor et al. |
| 2007/0270631 A1 | 11/2007 | Nelson et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0033431 A1 | 2/2008 | Jung et al. |
| 2008/0051784 A1 | 2/2008 | Gollogly |
| 2008/0051895 A1 | 2/2008 | Malandain et al. |
| 2008/0058936 A1 | 3/2008 | Malandain et al. |

(56) References Cited

U.S. PATENT DOCUMENTS

| | | |
|---|---|---|
| 2008/0058937 A1 | 3/2008 | Malandain et al. |
| 2008/0065077 A1 | 3/2008 | Ferree |
| 2008/0065215 A1 | 3/2008 | Reiley |
| 2008/0066764 A1 | 3/2008 | Paraschac et al. |
| 2008/0071275 A1 | 3/2008 | Ferree |
| 2008/0071276 A1 | 3/2008 | Ferree |
| 2008/0082118 A1 | 4/2008 | Edidin et al. |
| 2008/0082167 A1 | 4/2008 | Edidin et al. |
| 2008/0083413 A1 | 4/2008 | Forsell |
| 2008/0086128 A1 | 4/2008 | Lewis |
| 2008/0091059 A1 | 4/2008 | Machold et al. |
| 2008/0097523 A1 | 4/2008 | Bolduc et al. |
| 2008/0108995 A1 | 5/2008 | Conway et al. |
| 2008/0140188 A1 | 6/2008 | Rahdert et al. |
| 2008/0147139 A1 | 6/2008 | Barrett et al. |
| 2008/0147192 A1 | 6/2008 | Edidin et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0195156 A1 | 8/2008 | Ainsworth et al. |
| 2008/0226563 A1 | 9/2008 | Contag et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275552 A1 | 11/2008 | Makower et al. |
| 2008/0275555 A1 | 11/2008 | Makower et al. |
| 2008/0275557 A1 | 11/2008 | Makower et al. |
| 2008/0275567 A1 | 11/2008 | Makower et al. |
| 2008/0293995 A1 | 11/2008 | Moaddeb et al. |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112207 A1* | 4/2009 | Walker ............... A61B 17/7016 606/57 |
| 2009/0118699 A1 | 5/2009 | Utley et al. |
| 2009/0171356 A1 | 7/2009 | Klett |
| 2009/0177203 A1 | 7/2009 | Reiley |
| 2009/0182356 A1 | 7/2009 | Coe |
| 2009/0192514 A1 | 7/2009 | Feinberg et al. |
| 2009/0198144 A1 | 8/2009 | Phillips et al. |
| 2009/0204055 A1 | 8/2009 | Lennox et al. |
| 2009/0216113 A1 | 8/2009 | Meier et al. |
| 2009/0216262 A1 | 8/2009 | Burnett et al. |
| 2009/0240173 A1 | 9/2009 | Hsia et al. |
| 2009/0259236 A2 | 10/2009 | Burnett et al. |
| 2009/0270871 A1 | 10/2009 | Liu et al. |
| 2009/0275984 A1 | 11/2009 | Kim et al. |
| 2009/0318919 A1 | 12/2009 | Robinson |
| 2010/0004654 A1 | 1/2010 | Schmitz et al. |
| 2010/0030281 A1 | 2/2010 | Gollogly |
| 2010/0057127 A1 | 3/2010 | McGuire et al. |
| 2010/0081868 A1 | 4/2010 | Moaddeb et al. |
| 2010/0100185 A1 | 4/2010 | Trieu et al. |
| 2010/0106192 A1 | 4/2010 | Barry |
| 2010/0106193 A1 | 4/2010 | Barry |
| 2010/0114103 A1 | 5/2010 | Harrison et al. |
| 2010/0121323 A1* | 5/2010 | Pool ................... A61B 17/7004 606/54 |
| 2010/0121457 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0179601 A1 | 7/2010 | Jung et al. |
| 2010/0198261 A1 | 8/2010 | Trieu et al. |
| 2010/0228167 A1 | 9/2010 | Ilovich et al. |
| 2010/0241168 A1 | 9/2010 | Franck et al. |
| 2010/0249782 A1* | 9/2010 | Durham ............... A61B 5/06 606/62 |
| 2010/0249839 A1 | 9/2010 | Alamin et al. |
| 2010/0249847 A1 | 9/2010 | Jung et al. |
| 2010/0256626 A1 | 10/2010 | Muller et al. |
| 2010/0274290 A1 | 10/2010 | Jung et al. |
| 2010/0286730 A1 | 11/2010 | Gordon |
| 2010/0286791 A1 | 11/2010 | Goldsmith |
| 2010/0318129 A1 | 12/2010 | Seme et al. |
| 2010/0324684 A1 | 12/2010 | Eisermann et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060422 A1 | 3/2011 | Makower et al. |
| 2011/0098748 A1 | 4/2011 | Jangra |
| 2011/0130702 A1 | 6/2011 | Stergiopulos |
| 2011/0184505 A1 | 7/2011 | Sharkawy et al. |
| 2011/0196371 A1 | 8/2011 | Forsell |
| 2011/0196435 A1 | 8/2011 | Forsell |
| 2011/0202138 A1 | 8/2011 | Shenoy et al. |
| 2011/0257655 A1 | 10/2011 | Copf, Jr. |
| 2011/0275879 A1 | 11/2011 | Nelson et al. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0089186 A1 | 4/2012 | Carl et al. |
| 2012/0089191 A1 | 4/2012 | Altarac et al. |
| 2012/0109207 A1 | 5/2012 | Trieu |
| 2012/0116522 A1 | 5/2012 | Makower et al. |
| 2012/0116535 A1 | 5/2012 | Ratron et al. |
| 2012/0130426 A1 | 5/2012 | Thompson |
| 2012/0136449 A1 | 5/2012 | Makower et al. |
| 2012/0172883 A1 | 7/2012 | Sayago |
| 2012/0179273 A1 | 7/2012 | Clifford et al. |
| 2012/0185040 A1 | 7/2012 | Rahdert et al. |
| 2012/0221101 A1 | 8/2012 | Moaddeb et al. |
| 2012/0271353 A1 | 10/2012 | Barry |
| 2012/0277747 A1 | 11/2012 | Keller |
| 2012/0296234 A1 | 11/2012 | Wilhelm et al. |
| 2012/0312307 A1 | 12/2012 | Paraschac et al. |
| 2013/0013066 A1 | 1/2013 | Landry et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0079830 A1 | 3/2013 | Garamszegi et al. |
| 2013/0138017 A1 | 5/2013 | Jundt et al. |
| 2013/0138154 A1 | 5/2013 | Reiley |
| 2013/0150889 A1 | 6/2013 | Fening et al. |
| 2013/0178903 A1 | 7/2013 | Abdou |
| 2013/0197639 A1 | 8/2013 | Clifford et al. |
| 2013/0204266 A1 | 8/2013 | Heilman |
| 2013/0204376 A1 | 8/2013 | DiSilvestro et al. |
| 2013/0238094 A1 | 9/2013 | Voellmicke et al. |
| 2013/0253587 A1 | 9/2013 | Carls et al. |
| 2013/0261623 A1 | 10/2013 | Voellmicke et al. |
| 2013/0261672 A1 | 10/2013 | Horvath |
| 2013/0296863 A1 | 11/2013 | Globerman et al. |
| 2013/0325006 A1 | 12/2013 | Michelinie et al. |
| 2013/0325071 A1 | 12/2013 | Niemiec et al. |
| 2013/0331889 A1 | 12/2013 | Alamin et al. |
| 2013/0345802 A1 | 12/2013 | Cartledge et al. |
| 2014/0018913 A1 | 1/2014 | Cartledge et al. |
| 2014/0031826 A1 | 1/2014 | Bojarski et al. |
| 2014/0031929 A1 | 1/2014 | Cartledge et al. |
| 2014/0039558 A1 | 2/2014 | Alamin et al. |
| 2014/0051914 A1 | 2/2014 | Fobi et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0067075 A1 | 3/2014 | Makower et al. |
| 2014/0080203 A1 | 3/2014 | Wan et al. |
| 2014/0107704 A1 | 4/2014 | Serhan et al. |
| 2014/0135838 A1 | 5/2014 | Alamin et al. |
| 2014/0142698 A1 | 5/2014 | Landry et al. |
| 2014/0163664 A1 | 6/2014 | Goldsmith |
| 2014/0172097 A1 | 6/2014 | Clifford et al. |
| 2014/0194932 A1 | 7/2014 | Bruneau et al. |
| 2014/0222138 A1 | 8/2014 | Machold et al. |
| 2014/0296918 A1 | 10/2014 | Fening et al. |
| 2014/0303539 A1 | 10/2014 | Baym et al. |

(56) References Cited

U.S. PATENT DOCUMENTS

| | | | |
|---|---|---|---|
| 2014/0303540 A1 | 10/2014 | Baym et al. |
| 2014/0336756 A1 | 11/2014 | Lee et al. |
| 2014/0358150 A1 | 12/2014 | Kaufman et al. |
| 2015/0013687 A1 | 1/2015 | Paraschac et al. |
| 2015/0057490 A1 | 2/2015 | Forsell |
| 2015/0073565 A1 | 3/2015 | Nelson et al. |
| 2015/0105782 A1 | 4/2015 | D'Lima et al. |
| 2015/0105824 A1 | 4/2015 | Moskowitz et al. |
| 2015/0132174 A1 | 5/2015 | Marinescu et al. |
| 2015/0134007 A1 | 5/2015 | Alamin et al. |
| 2015/0142110 A1 | 5/2015 | Myers et al. |
| 2015/0150561 A1 | 6/2015 | Burnett et al. |
| 2015/0272600 A1 | 10/2015 | Mehta et al. |
| 2015/0313649 A1 | 11/2015 | Alamin et al. |

FOREIGN PATENT DOCUMENTS

| | | |
|---|---|---|
| DE | 1541262 | 6/1969 |
| DE | 8515687 | 12/1985 |
| DE | 68515687.6 | 12/1985 |
| DE | 19626230 | 1/1998 |
| DE | 19751733 | 12/1998 |
| DE | 19745654 | 4/1999 |
| DE | 102005045070 | 4/2007 |
| DE | 102007053362 | 5/2009 |
| EP | 0663184 | 7/1995 |
| EP | 1547549 | 6/2005 |
| EP | 1745765 | 1/2007 |
| EP | 1905388 | 4/2008 |
| FR | 2802406 | 6/2001 |
| FR | 2823663 | 10/2002 |
| FR | 2827756 | 1/2003 |
| FR | 2892617 | 5/2007 |
| FR | 2900563 | 11/2007 |
| FR | 2901991 | 12/2007 |
| FR | 2916622 | 12/2008 |
| FR | 2961386 | 12/2011 |
| GB | 1174814 | 12/1969 |
| HU | 223454 | 4/2002 |
| JP | 05-104022 | 4/1993 |
| JP | 09-056736 | 3/1997 |
| JP | 2001-507608 | 6/2001 |
| JP | 2003-172372 | 6/2003 |
| JP | 2003-530195 | 10/2003 |
| JP | 2007-050339 | 3/2007 |
| WO | WO8604498 | 8/1986 |
| WO | WO8707134 | 12/1987 |
| WO | WO8906940 | 8/1989 |
| WO | WO9601597 | 1/1996 |
| WO | WO9808454 | 3/1998 |
| WO | WO9830163 | 7/1998 |
| WO | WO1998044858 | 10/1998 |
| WO | WO9850309 | 11/1998 |
| WO | WO9903348 | 1/1999 |
| WO | WO9923744 | 5/1999 |
| WO | WO9951160 | 10/1999 |
| WO | WO1999051160 | 10/1999 |
| WO | WO9963907 | 12/1999 |
| WO | WO0000108 | 1/2000 |
| WO | WO0072768 | 12/2000 |
| WO | WO0105463 | 1/2001 |
| WO | WO0112108 | 2/2001 |
| WO | WO0124742 | 4/2001 |
| WO | WO2001024697 | 4/2001 |
| WO | WO0141671 | 6/2001 |
| WO | WO0145485 | 6/2001 |
| WO | WO0145487 | 6/2001 |
| WO | WO0145597 | 6/2001 |
| WO | WO0158390 | 8/2001 |
| WO | WO0167973 | 9/2001 |
| WO | WO0178614 | 10/2001 |
| WO | WO0236975 | 5/2002 |
| WO | WO03059215 | 7/2003 |
| WO | WO2004014245 | 2/2004 |
| WO | WO2004019796 | 3/2004 |
| WO | WO2004021870 | 3/2004 |
| WO | WO2004043280 | 5/2004 |
| WO | WO2005023090 | 3/2005 |
| WO | WO2005072195 | 8/2005 |
| WO | WO2005072664 | 8/2005 |
| WO | WO2005105001 | 11/2005 |
| WO | WO2006019520 | 2/2006 |
| WO | WO2006019521 | 2/2006 |
| WO | WO2006089085 | 8/2006 |
| WO | WO2006090380 | 8/2006 |
| WO | WO2006090380 | 10/2006 |
| WO | WO2006103071 | 10/2006 |
| WO | WO2006103074 | 10/2006 |
| WO | WO2006105084 | 10/2006 |
| WO | WO2007013059 | 2/2007 |
| WO | WO2007015239 | 2/2007 |
| WO | WO2007025191 | 3/2007 |
| WO | WO2007048012 | 4/2007 |
| WO | WO2007081304 | 7/2007 |
| WO | WO2007118179 | 10/2007 |
| WO | WO2007140180 | 12/2007 |
| WO | WO2007149555 | 12/2007 |
| WO | WO20071144489 | 12/2007 |
| WO | WO2008003952 | 1/2008 |
| WO | WO2008013623 | 1/2008 |
| WO | WO2008015679 | 2/2008 |
| WO | WO2008040880 | 4/2008 |
| WO | WO2008140756 | 11/2008 |
| WO | WO2010017649 | 2/2010 |
| WO | WO2010050891 | 5/2010 |
| WO | WO2010056650 | 5/2010 |
| WO | WO2011018778 | 2/2011 |
| WO | WO2011116158 | 9/2011 |
| WO | WO2013119528 | 8/2013 |
| WO | WO2013181329 | 12/2013 |
| WO | WO2014040013 | 3/2014 |
| WO | WO2011041398 | 4/2015 |

OTHER PUBLICATIONS

Abe, Jun, Kensei Nagata, Mamoru Ariyoshi, and Akio Inoue. "Experimental external fixation combined with percutaneous discectomy in the management of scoliosis." Spine 24, No. 7 (1999): 646-653.

Amer, A. R. A. L., and Ashraf A. Khanfour. "Evaluation of treatment of late-onset tibia vara using gradual angulationtranslation high tibial osteotomy." Acta orthopaedica Belgica 76, No. 3 (2010): 360.

Baumgart, Rainer, Stefan Hinterwimmer, Michael Krammer, Oliver Muensterer, and Wolf Mutschler. "The bioexpandable prosthesis: a new perspective after resection of malignant bone tumors in children." Journal of pediatric hematology/oncology 27, No. 8 (2005): 452-455.

Baumgart, R., P. Thaller, S. Hinterwimmer, M. Krammer, T. Hierl, and W. Mutschler. "A fully implantable, programmable distraction nail (Fitbone)—new perspectives for corrective and reconstructive limb surgery." In Practice of Intramedullary Locked Nails, pp. 189-198. Springer Berlin Heidelberg, 2006.

Bodó, László, László Hangody, Balázs Borsitzky, György Béres, Gabriella Arató, Péter Nagy, and Gábor K. Ráthonyi. "Development of a tension-adjustable implant for anterior cruciate ligament reconstruction." Eklem Hast Cerrahisi 19, No. 1 (2008): 27-32.

Boudjemline, Younes, Emmanuelle Pineau, Caroline Bonnet, Alix Mollet, Sylvia Abadir, Damien Bonnet, Daniel Sidi, and Gabriella Agnoletti. "Off-label use of an adjustable gastric banding system for pulmonary artery banding." The Journal of thoracic and cardiovascular surgery 131, No. 5 (2006): 1130-1135.

Brochure—VEPTR II Technique Guide Apr. 2008.

Brochure—VEPTR Patient Guide dated Feb. 2005.

Brown, S. "Single Port Surgery and the Dundee Endocone." SAGES Annual Scientific Sessions, Poster Abstracts (2007): 323-324.

Buchowski, Jacob M., Rishi Bhatnagar, David L. Skaggs, and Paul D. Sponseller. "Temporary internal distraction as an aid to correction of severe scoliosis." The Journal of Bone & Joint Surgery 88, No. 9 (2006): 2035-2041.

Burghardt, R. D., J. E. Herzenberg, S. C. Specht, and D. Paley. "Mechanical failure of the Intramedullary Skeletal Kinetic Distractor in limb lengthening." Journal of Bone & Joint Surgery, British vol. 93, No. 5 (2011): 639-643.

(56) References Cited

OTHER PUBLICATIONS

Burke, John Gerard. "Design of a minimally invasive non fusion device for the surgical management of scoliosis in the skeletally immature." Studies in health technology and informatics 123 (2005): 378-384.
Carter, D. R., and W. E. Caler. "A cumulative damage model for bone fracture." Journal of Orthopaedic Research 3, No. 1 (1985): 84-90.
Chapman, Andrew E., George Kiroff, Philip Game, Bruce Foster, Paul O'Brien, John Ham, and Guy J. Maddern. "Laparoscopic adjustable gastric banding in the treatment of obesity: a systematic literature review." Surgery 135, No. 3 (2004): 326-351.
Cole, J. Dean, Daniel Justin, Tagus Kasparis, Derk DeVlught, and Carl Knobloch. "The intramedullary skeletal distractor (ISKD): first clinical results of a new intramedullary nail for lengthening of the femur and tibia." Injury 32 (2001):129-139.
Cole, J., D. Paley, and M. Dahl. "Operative Technique. ISKD. Intramedullary Skeletal Kinetic Distractor. Tibial Surgical Technique." IS-0508 (A)-OPT-US © Orthofix Inc 28 (2005).
Dailey, Hannah L., Charles J. Daly, John G. Galbraith, Michael Cronin, and James A. Harty. "A novel intramedullary nail for micromotion stimulation of tibial fractures." Clinical Biomechanics 27, No. 2 (2012): 182-188.
Daniels, A. U., Patrick Gemperline, Allen R. Grahn, and Harold K. Dunn. "A new method for continuous intraoperative measurement of Harrington rod loading patterns." Annals of biomedical engineering 12, No. 3 (1984): 233-246.
De Giorgi, G., G. Stella, S. Becchetti, G. Martucci, and D. Miscioscia. "Cotrel-Dubousset instrumentation for the treatment of severe scoliosis." European Spine Journal 8, No. 1 (1999): 8-15.
Dorsey, W. O., Bruce S. Miller, Jared P. Tadje, and Can R. Bryant. "The stability of three commercially available implants used in medial opening wedge high tibial osteotomy." The journal of knee surgery 19, No. 2 (2006): 95-98.
Edeland, H. G., G. Eriksson, and E. Dahlberg. "Instrumentation for distraction by limited surgery in scoliosis treatment." Journal of biomedical engineering 3, No. 2 (1981): 143-146.
Ember, T., and H. Noordeen. "Distraction forces required during growth rod lengthening." Journal of Bone & Joint Surgery, British vol. 88, No. Supp II (2006): 229-229.
Fabry, Hans, Robrecht Van Hee, Leo Hendrickx, and Eric Totté. "A technique for prevention of port adjustable silicone gastric banding." Obesity surgery 12, No. 2 (2002): 285-288.
Fried, M., W. Lechner, and K. Kormanova. "In vivo measurements of different gastric band pressures towards the gastric wall at the stoma region." In Obesity Surgery, vol. 14, No. 7, pp. 914-914. 3100 Bayview Ave, Unit 4, Toronto, Ontario M2N 5L3, Canada: F D-Communications Inc, 2004.
Gao, Xiaochong, Derek Gordon, Dongping Zhang, Richard Browne, Cynthia Helms, Joseph Gillum, Samuel Weber et al. "CHD7 gene polymorphisms are associated with susceptibility to idiopathic scoliosis." The American Journal of Human Genetics 80, No. 5 (2007): 957-965.
Gebhart, M., M. Neel, A. Soubeiran, and J. Dubousset. "Early clinical experience with a custom made growing endoprosthesis in children with malignant bone tumors of the lower extremity actioned by an external permanent magnet: the Phenix M system." In International Society of Limb Salvage 14th International Symposium on Limb Salvage.2007.
Gillespie, R., and J. Obrien. "Harrington instrumentation without fusion." In Journal of Bone and Joint SurgeryBritish Volume, vol. 63, No. 3, pp. 461-461. 22 Buckingham Street, London, England WC2N 6ET: British Editorial Soc Bone Joint Surgery, 1981.
Goodship, Allen E., James L. Cunningham, and John Kenwright. "Strain rate and timing of stimulation in mechanical modulation of fracture healing." Clinical orthopaedics and related research 355 (1998): S105-S115.
Grass, P. Jose, A. Valentin Soto, and H. Paula Araya. "Intermittent distracting rod for correction of high neurologic risk congenital scoliosis." Spine 22, No. 16 (1997): 1922-1927.

Gray's Anatomy, http://education.yahoo.com/reference/gray/subjects/subject/128, published Jul. 1, 2007.
Grimer, R., S. Carter, R. Tillman, A. Abudu, and L. Jeys. "Non-Invasive Extendable Endoprostheses for Children—Expensive but Worth it!." Journal of Bone & Joint Surgery, British vol. 93, No. Supp I (2011): 5-5.
Grünert, R. D. "[The development of a totally implantable electronic sphincter]." Langenbecks Archiv fur Chirurgie 325 (1968): 1170-1174.
Guichet, Jean-Marc, Barbara Deromedis, Leo T. Donnan, Giovanni Peretti, Pierre Lascombes, and Flavio Bado. "Gradual femoral lengthening with the Albizzia intramedullary nail." The Journal of Bone & Joint Surgery 85, No. 5 (2003): 838-848.
Gupta, A., J. Meswania, R. Pollock, S. R. Cannon, T. W. R. Briggs, S. Taylor, and G. Blunn. "Non-invasive distal femoral expandable endoprosthesis for limb-salvage surgery in paediatric tumours." Journal of Bone & Joint Surgery, British vol. 88, No. 5 (2006): 649-654.
Hankemeier S, Gösling T, Pape HC, et al. Limb lengthening with the Intramedullary Skeletal Kinetic Distractor (ISKD) Oper Orthop Traumatol. 2005;17:79-101.
Harrington PR (1962) Treatment of scoliosis. Correction and internal fixation by spine instrumentation. J Bone Joint Surg Am 44-A:591-610.
Hazem Elsebaie, M. D. "Single Growing Rods." Changing the Foundations: Does it affect the Results., J Child Orthop. (2007) 1:258.
Hennig, Alex C.; Incavo, Stephen J.; Beynnon, Bruce D.; Abate, Joseph A.; Urse, John S.; Kelly, Stephen / The safety and efficacy of a new adjustable plate used for proximal tibial opening wedge osteotomy in the treatment of unicompartmental knee osteoarthrosis. In: The journal of knee surgery, vol. 20, No. 1, Jan. 1, 2007, p. 6-14.
Hofmeister, M., C. Hierholzer, and V. Bühren. "Callus Distraction with the Albizzia Nail." In Practice of Intramedullary Locked Nails, pp. 211-215. Springer Berlin Heidelberg, 2006.
Horbach, T., D. Herzog, and I. Knerr. "First experiences with the routine use of the Rapid Port (TM) system with the Lap-Band (R)." In Obesity Surgery, vol. 16, No. 4, pp. 418-418. 3100 Bayview Ave, Unit 4, Toronto, Ontario M2N 5L3, Canada: F D-Communications Inc, 2006.
Hyodo, Akira, Helmuth Kotschi, Helen Kambic, and George Muschler. "Bone transport using intramedullary fixation and a single flexible traction cable." Clinical orthopaedics and related research 325 (1996): 256-268.
Ahlbom, A., U. Bergqvist, J. H. Bernhardt, J. P. Cesarini, M. Grandolfo, M. Hietanen, A. F. Mckinlay et al. "Guidelines for limiting exposure to time-varying electric, magnetic, and electromagnetic fields (up to 300 GHz). International Commission on Non-Ionizing Radiation Protection." Health Phys 74, No. 4 (1998): 494-522.
International Commission on Non-Ionizing Radiation Protection. "Guidelines on limits of exposure to static magnetic fields." Health Physics 96, No. 4 (2009): 504-514.
INVIS®/Lamello Catalog, 2006, Article No. 68906A001 GB.
Kasliwal, Manish K., Justin S. Smith, Adam Kanter, Ching-Jen Chen, Praveen V. Mummaneni, Robert A. Hart, and Christopher I. Shaffrey. "Management of high-grade spondylolisthesis." Neurosurgery Clinics of North America 24, No. 2 (2013): 275-291.
Kenawey, Mohamed, Christian Krettek, Emmanouil Liodakis, Ulrich Wiebking, and Stefan Hankemeier. "Leg lengthening using intramedullay skeletal kinetic distractor: results of 57 consecutive applications." Injury 42, No. 2 (2011): 150-155.
Kent, Matthew E., Arvind Arora, P. Julian Owen, and Vikas Khanduja. "Assessment and correction of femoral malrotation following intramedullary nailing of the femur." Acta Orthop Belg 76, No. 5 (2010): 580-4.
Klemme, William R., Francis Denis, Robert B. Winter, John W. Lonstein, and Steven E. Koop. "Spinal instrumentation without fusion for progressive scoliosis in young children." Journal of Pediatric Orthopaedics 17, No. 6 (1997): 734-742.
Korenkov, M., S. Sauerland, N. Yücel, L. Köhler, P. Goh, J. Schierholz, and H. Troidl. "Port function after laparoscopic adjust-

(56) References Cited

OTHER PUBLICATIONS able gastric banding for morbid obesity." Surgical Endoscopy and Other Interventional Techniques 17, No. 7 (2003): 1068-1071.

Krieg, Andreas H., Bernhard M. Speth, and Bruce K. Foster. "Leg lengthening with a motorized nail in adolescents." Clinical orthopaedics and related research 466, No. 1 (2008): 189-197.

Kucukkaya, Metin, Raffi Armagan, and Unal Kuzgun. "The new intramedullary cable bone transport technique." Journal of orthopaedic trauma 23, No. 7 (2009): 531-536.

Lechner, W. L., W. Kirchmayr, and G. Schwab. "In vivo band manometry: a new method in band adjustment." In Obesity Surgery, vol. 15, No. 7, pp. 935-935. 3100 Bayview Ave, Unit 4, Toronto, Ontario M2N 5L3, Canada: F DCommunicationsinc, 2005.

Lechner, W., M. Gadenstatter, R. Ciovica, W. Kirchmayer, and G. Schwab. "Intra-band manometry for band adjustments: The basics." In Obesity Surgery, vol. 16, No. 4, pp. 417-418. 3100 Bayview Ave, Unit 4, Toronto, Ontario M2N 5L3, Canada: F D-Communications Inc, 2006.

Li, G., S. Berven, N. A. Athanasou, and A. H. R. W. Simpson. "Bone transport over an intramedullary nail: A case report with histologic examination of the regenerated segment." Injury 30, No. 8 (1999): 525-534.

Lonner, Baron S. "Emerging minimally invasive technologies for the management of scoliosis." Orthopedic Clinics of North America 38, No. 3 (2007): 431-440.

Teli, Marco MD. "Measurement of Forces Generated During Distraction of Growing Rods, J." Marco Teli. Journal of Child Orthop 1 (2007): 257-258.

Matthews, Michael Wayne, Harry Conrad Eggleston, Steven D. Pekarek, and Greg Eugene Hilmas. "Magnetically adjustable intraocular lens." Journal of Cataract & Refractive Surgery 29, No. 11 (2003): 2211-2216.

Micromotion "Micro Drive Engineering•General catalogue" pp. 14.24; Jun. 2009.

Mineiro, Jorge, and Stuart L. Weinstein. "Subcutaneous rodding for progressive spinal curvatures: early results." Journal of Pediatric Orthopaedics 22, No. 3 (2002): 290-295.

Moe, John H., Khalil Kharrat, Robert B. Winter, and John L. Cummine. "Harrington instrumentation without fusion plus external orthotic support for the treatment of difficult curvature problems in young children." Clinical orthopaedics and related research 185 (1984): 35-45.

Montague, R. G., C. M. Bingham, and K. Atallah. "Magnetic gear dynamics for servo control." In MELECON 2010-2010 15th IEEE Mediterranean Electrotechnical Conference, pp. 1192-1197. IEEE, 2010.

Montague, Ryan, Chris Bingham, and Kais Atallah. "Servo control of magnetic gears." Mechatronics, IEEE/ASME Transactions on 17, No. 2 (2012): 269-278.

Nachemson, Alf, and Gösta Elfström. "Intravital wireless telemetry of axial forces in Harrington distraction rods in patients with idiopathic scoliosis." The Journal of Bone & Joint Surgery 53, No. 3 (1971): 445-465.

Nachlas, I. William, and Jesse N. Borden. "The cure of experimental scoliosis by directed growth control." The Journal of Bone & Joint Surgery 33, No. 1 (1951): 24-34.

Newton, P. "Fusionless Scoliosis Correction by Anterolateral Tethering . . . Can it Work?." In 39th Annual Scoliosis Research Society Meeting. 2004.

Observations by a third party under Article 115 EPC issued by the European Patent Office dated Feb. 15, 2010 in European Patent Application No. 08805612.2, Applicant: Soubeiran, Arnaud (7 pages).

Oh, Chang-Wug, Hae-Ryong Song, Jae-Young Roh, Jong-Keon Oh, Woo-Kie Min, Hee-Soo Kyung, Joon-Woo Kim, Poong-Taek Kim, and Joo-Chul Ihn. "Bone transport over an intramedullary nail for reconstruction of long bone defects in tibia." Archives of orthopaedic and trauma surgery 128, No. 8 (2008): 801-808.

Ozcivici, Engin, Yen Kim Luu, Ben Adler, Yi-Xian Qin, Janet Rubin, Stefan Judex, and Clinton T. Rubin. "Mechanical signals as anabolic agents in bone." Nature Reviews Rheumatology 6, No. 1 (2010): 50-59.

Patient Guide, VEPTR Vertical Expandable Prosthetic Titanium Rib, Synthes Spine (2005) (23pages).

Piorkowski, James R., Scott J. Ellner, Arun A. Mavanur, and Carlos A. Barba. "Preventing port site inversion in laparoscopic adjustable gastric banding." Surgery for Obesity and Related Diseases 3, No. 2 (2007): 159-161.

Prontes, Isabel, http://wwwehow.com/about_4795793_longest-bone-body.html, published Jun. 12, 2012.

Rathjen, Karl, Megan Wood, Anna McClung, and Zachary Vest. "Clinical and radiographic results after implant removal in idiopathic scoliosis." Spine 32, No. 20 (2007): 2184-2188.

Ren, Christine J., and George A. Fielding. "Laparoscopic adjustable gastric banding: surgical technique." Journal of Laparoendoscopic & Advanced Surgical Techniques 13, No. 4 (2003): 257-263.

Reyes-Sánchez, Alejandro, Luis Miguel Rosales, and Víctor Miramontes. "External fixation for dynamic correction of severe scoliosis." The Spine Journal 5, No. 4 (2005): 418-426.

Rinsky, Lawrence A., James G. Gamble, and Eugene E. Bleck. "Segmental Instrumentation Without Fusion in Children With Progressive Scoliosis." Journal of Pediatric Orthopedics 5, No. 6 (1985): 687-690.

Rode, V., F. Gay, A. J. Baraza, and J. Dargent. "A simple way to adjust bands under radiologic control." In Obesity Surgery, vol. 16, No. 4, pp. 418-418. 3100 Bayview Ave, Unit 4, Toronto, Ontario M2N 5L3, Canada: F Dcommunications Inc, 2006.

Schmerling, M. A., M. A. Wilkov, A. E. Sanders, and J. E. Woosley. "Using the shape recovery of nitinol in the Harrington rod treatment of scoliosis." Journal of biomedical materials research 10, No. 6 (1976): 879-892.

Scott, D. J., S. J. Tang, R. Fernandez, R. Bergs, and J. A. Cadeddu. "Transgastric, transcolonic, and transvaginal cholecystectomy using magnetically anchored instruments." In SAGES Meeting, p. P511. 2007.

Sharke, Paul. "The machinery of life." Mechanical Engineering 126, No. 2 (2004): 30.

Shiha, Anis, Mohamed Alam El-Deen, Abdel Rahman Khalifa, and Mohamed Kenawey. "Ilizarov gradual correction of genu varum deformity in adults." Acta Orthop Belg 75 (2009): 784-91.

Simpson, A. H. W. R., H. Shalaby, and G. Keenan. "Femoral lengthening with the intramedullary skeletal kinetic distractor." Journal of Bone & Joint Surgery, British vol. 91, No. 7 (2009): 955-961.

Smith, John T. "The use of growth-sparing instrumentation in pediatric spinal deformity." Orthopedic Clinics of North America 38, No. 4 (2007): 547-552.

Soubeiran, A., M. Gebhart, L. Miladi, J. Griffet, M. Neel, and J. Dubousset. "The Phenix M System. A Mechanical Fully Implanted Lengthening Device Externally Controllable Through the Skin with a Palm Size Permanent Magnet; Applications to Pediatric Orthopaedics." In 6th European Research Conference in Pediatric Orthopaedics 2006.

Sun, Zongyang, Katherine L. Rafferty, Mark A. Egbert, and Susan W. Herring. "Masticatory mechanics of a mandibular distraction osteogenesis site: interfragmentary micromovement." Bone 41, No. 2 (2007): 188-196.

Takaso, Masashi, Hideshige Moriya, Hiroshi Kitahara, Shohei Minami, Kazuhisa Takahashi, Keijiro Isobe, Masatsune Yamagata, Yoshinori Otsuka, Yoshinori Nakata, and Masatoshi Inoue. "New remote-controlled growing-rod spinal instrumentation possibly applicable for scoliosis in young children." Journal of orthopaedic science 3, No. 6 (1998): 336-340.

Tello, Carlos A. "Harrington instrumentation without arthrodesis and consecutive distraction program for young children with severe spinal deformities. Experience and technical details." The Orthopedic clinics of North America 25, No. 2 (1994): 333-351.

Thaller, Peter Helmut, Julian Fürmetz, Florian Wolf, Thorsten Eilers, and Wolf Mutschler. "Limb lengthening with fully implantable magnetically actuated mechanical nails (PHENIX®)—Preliminary results." Injury 45 (2014): S60-S65.

(56) References Cited

OTHER PUBLICATIONS

Thompson, George H., Lawrence G. Lenke, Behrooz A. Akbarnia, Richard E. McCarthy, and Robert M. Campbell. "Early onset scoliosis: future directions." The Journal of Bone & Joint Surgery 89, No. suppl 1 (2007): 163-166.

Thonse, Raghuram, John E. Herzenberg, Shawn C. Standard, and Dror Paley. "Limb lengthening with a fully implantable, telescopic, intramedullary nail." Operative Techniques in Orthopedics 15, No. 4 (2005): 355-362.

Trias, A., P. Bourassa, and M. Massoud. "Dynamic loads experienced in correction of idiopathic scoliosis using two types of Harrington rods." Spine 4, No. 3 (1978): 228-235.

VEPTR II. Vertical Expandable Prosthetic Titanium Rib II, Technique Guide, Systhes Spine (2008) (40 pages).

Verkerke, G. J., Koops H. Schraffordt, R. P. Veth, H. J. Grootenboer, L. J. De Boer, J. Oldhoff, and A. Postma. "Development and test of an extendable endoprosthesis for bone reconstruction in the leg." The International journal of artificial organs 17, No. 3 (1994): 155-162.

Verkerke, G. J., H. Schraffordt Koops, R. P. H. Veth, J. Oldhoff, H. K. L. Nielsen, H. H. Van den Kroonenberg, H. J. Grootenboer, and F. M. Van Krieken. "Design of a lengthening element for a modular femur endoprosthetic system." Proceedings of the Institution of Mechanical Engineers, Part H: Journal of Engineering in Medicine 203, No. 2 (1989): 97-102.

Verkerke, G. J., H. Schraffordt Koops, R. P. H. Veth, H. H. van den Kroonenberg, H. J. Grootenboer, H. K. L. Nielsen, J. Oldhoff, and A. Postma. "An extendable modular endoprosthetic system for bone tumour management in the leg." Journal of biomedical engineering 12, No. 2 (1990): 91-96.

Weiner, Rudolph A., Michael Korenkov, Esther Matzig, Sylvia Weiner, and Woiteck K. Karcz. "Initial clinical experience with telemetrically adjustable gastric banding." Surgical technology international 15 (2005): 63-69.

Wenger, H. L. "Spine Jack Operation in the Correction of Scoliotic Deformity: A Direct Intrathoracic Attack to Straighten the Laterally Bent Spine: Preliminary Report." Archives of Surgery 83, No. 6 (1961): 901-910.

White III, Augustus A., and Manohar M. Panjabi. "The clinical biomechanics of scoliosis." Clinical orthopaedics and related research 118 (1976): 100-112.

Yonnet, Jean-Paul. "Passive magnetic bearings with permanent magnets." Magnetics, IEEE Transactions on 14, No. 5 (1978): 803-805.

Yonnet, Jean-Paul. "A new type of permanent magnet coupling." Magnetics, IEEE Transactions on 17, No. 6 (1981): 2991-2993.

Zheng, Pan, Yousef Haik, Mohammad Kilani, and Ching-Jen Chen. "Force and torque characteristics for magnetically driven blood pump." Journal of Magnetism and Magnetic Materials 241, No. 2 (2002): 292-302.

\* cited by examiner

EXTERNAL ADJUSTMENT DEVICE FOR DISTRACTION DEVICE

RELATED APPLICATION

Any and all applications for which a foreign or domestic priority claim is identified in the Application Data Sheet as filed with the present application are hereby incorporated by reference under 37 CFR 1.57.

FIELD OF THE INVENTION

The field of the invention generally relates to medical devices for treating disorders of the skeletal system.

BACKGROUND

Scoliosis is a general term for the sideways (lateral) curving of the spine, usually in the thoracic or thoracolumbar region. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually followed up, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician, so often, the curve progresses rapidly and severely. There is a large population of grown adults with untreated scoliosis, in extreme cases with a Cobb angle as high as or greater than 90°, Many of these adults, though, do not have pain associated with this deformity, and live relatively normal lives, though oftentimes with restricted mobility and motion. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with hooks or bone screws, or more specifically pedicle screws, in a manner that allows the spine to be straightened. Usually, at the section desired for fusion, the intervertebral disks are removed and bone graft material is placed to create the fusion. If this is autologous material, the bone is harvested from a hip via a separate incision.

Alternatively, the fusion surgery may be performed anteriorly. A lateral and anterior incision is made for access. Usually, one of the lungs is deflated in order to allow access to the spine from this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and are secured to the vertebra on the anterior convex portion of the curve. Currently, clinical trials are being performed which use staples in place of the tether/screw combination. One advantage of this surgery in comparison with the posterior approach is that the scars from the incisions are not as dramatic, though they are still located in a visible area, when a bathing suit, for example, is worn. The staples have had some difficulty in the clinical trials. The staples tend to pull out of the bone when a critical stress level is reached.

In some cases, after surgery, the patient will wear a protective brace for a few months as the fusing process occurs. Once the patient reaches spinal maturity, it is difficult to remove the rods and associated hardware in a subsequent surgery, because the fusion of the vertebra usually incorporates the rods themselves. Standard practice is to leave this implant in for life. With either of these two surgical methods, after fusion, the patient's spine is now straight, but depending on how many vertebra were fused, there are often limitations in the degree of flexibility, both in bending and twisting. As these fused patients mature, the fused section can impart large stresses on the adjacent non-fused vertebra, and often, other problems including pain can occur in these areas, sometimes necessitating further surgery. This tends to be in the lumbar portion of the spine that is prone to problems in aging patients. Many physicians are now interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five, and more often in boys than in girls. This is a more rare condition, occurring in only about one or two out of 10,000 children, but can be severe, sometimes affecting the normal development of organs. Because of the fact that the spines of these children will still grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a rather high preponderance of infection.

Returning to the AIS patients, the treatment methodology for those with a Cobb angle between 20° and 40° is quite controversial. Many physicians proscribe a brace (for example, the Boston Brace), that the patient must wear on their body and under their clothes 18 to 23 hours a day until they become skeletally mature, for example to age 16. Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. It is commonly known that many patients have at times hidden their braces, for example, in a bush outside of school, in order to escape any related embarrassment. The patient compliance with brace wearing has been so problematic that there have been special braces constructed which sense the body of the patient, and keep track of the amount of time per day that the brace is worn. Patients have even been known to place objects into unworn braces of this type in order to fool the sensor. Coupled with the inconsistent patient compliance with brace usage, is a feeling by many physicians that braces, even if used properly, are not at all effective at curing scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment. Some say the reason for the supposed ineffectiveness of the brace is that it works only on a portion of the torso, and not on the entire spine. Currently a prospective, randomized 500 patient clinical trial known as BrAIST (Bracing in Adolescent Idiopathic Scoliosis Trial) is enrolling patients, 50% of whom will be treated with the brace and 50% of who will simply be watched. The Cobb angle data will be measured continually up until skeletal maturity, or until a Cobb angle of 50° is reached, at which time the patient will likely undergo surgery. Many physicians feel that the BrAIST trial will show that braces are completely ineffective. If this is the case, the quandary about what to do with AIS patients who have a Cobb angle of between 20° and 40° will only become more pronounced. It should be noted that the "20° to 40°" patient population is as much as ten times larger than the "40° and greater" patient population.

Distraction osteogenesis, also known as distraction calotasis and osteodistraction has been used successfully to lengthen long bones of the body. Typically, the bone, if not already fractured, is purposely fractured by means of a corticotomy, and the two segments of bone are gradually distracted apart, which allows new bone to form in the gap. If the distraction rate is too high, there is a risk of nonunion, if the rate is too low, there is a risk that the two segments will completely fuse to each other before the distraction period is complete. When the desired length of the bone is achieved using this process, the bone is allowed to consolidate. Distraction osteogenesis applications are mainly focused on the growth of the femur or tibia, but may also include the humerus, the jaw bone (micrognathia), or other bones. The reasons for lengthening or growing bones are multifold, the applications including, but not limited to: post osteosarcoma bone cancer; cosmetic lengthening (both legs-femur and/or tibia) in short stature or dwarfism/achondroplasia; length-ening of one limb to match the other (congenital, post-trauma, post-skeletal disorder, prosthetic knee joint), non-unions.

Distraction osteogenesis using external fixators has been done for many years, but the external fixator can be unwieldy for the patient. It can also be painful, and the patient is subject to the risk of pin track infections, joint stiffness, loss of appetite, depression, cartilage damage and other side effects. Having the external fixator in place also delays the beginning of rehabilitation.

In response to the shortcomings of external fixator distraction, intramedullary distraction nails have been surgically implanted which are contained entirely within the bone. Some are automatically lengthened via repeated rotation of the patient's limb. This can sometimes be painful to the patient, and can often proceed in an uncontrolled fashion. This therefore makes it difficult to follow the strict daily or weekly lengthening regime that avoids nonunion (if too fast) or early consolidation (if too slow). Lower limb distraction rates are on the order of one mm per day. Other intramedullary nails have been developed which have an implanted motor and are remotely controlled by an antenna. These devices are therefore designed to be lengthened in a controlled manner, but due to their complexity, may not be manufacturable as an affordable product. Others have proposed intramedullary distractors containing and implanted magnet, which allows the distraction to be driven electromagnetically by an external stator. Because of the complexity and size of the external stator, this technology has not been reduced to a simple and cost-effective device that can be taken home, to allow patients to do daily lenthenings.

SUMMARY

In one embodiment, an external adjustment device includes at least one permanent magnet configured for rotation about an axis. The external adjustment device further includes a first handle extending linearly at a first end of the device and a second handle disposed at a second end of the device, the second handle extending in a direction that is angled relative to the first handle. The external adjustment device includes a motor mounted inside the first handle and a first button located in the proximity to one of the first handle or the second handle, the first button configured to be operated by the thumb of a hand that grips the one of the first handle or second handle. The first button is configured to actuate the motor causing the at least one permanent magnet to rotate about the axis in a first direction.

In another embodiment, an external adjustment device includes at least one permanent magnet configured for rotation about an axis and a motor configured for rotating the at least one permanent magnet about the axis. The external adjustment device includes a first handle extending linearly at a first end of the device and a second handle disposed at a second end of the device, the second handle extending in a direction that is substantially off axis with respect to the first handle, wherein one of the first and second handle comprises a looped shape. A first drive button is located in the proximity to one of the first handle or the second handle, the first drive button configured to be operated by the thumb of a hand that grips the one of the first handle or second handle. The first drive button is configured to actuate the motor causing the at least one permanent magnet to rotate about the axis in a first direction.

DETAILED DESCRIPTION OF THE ILLUSTRATED EMBODIMENTS

Figure 1:
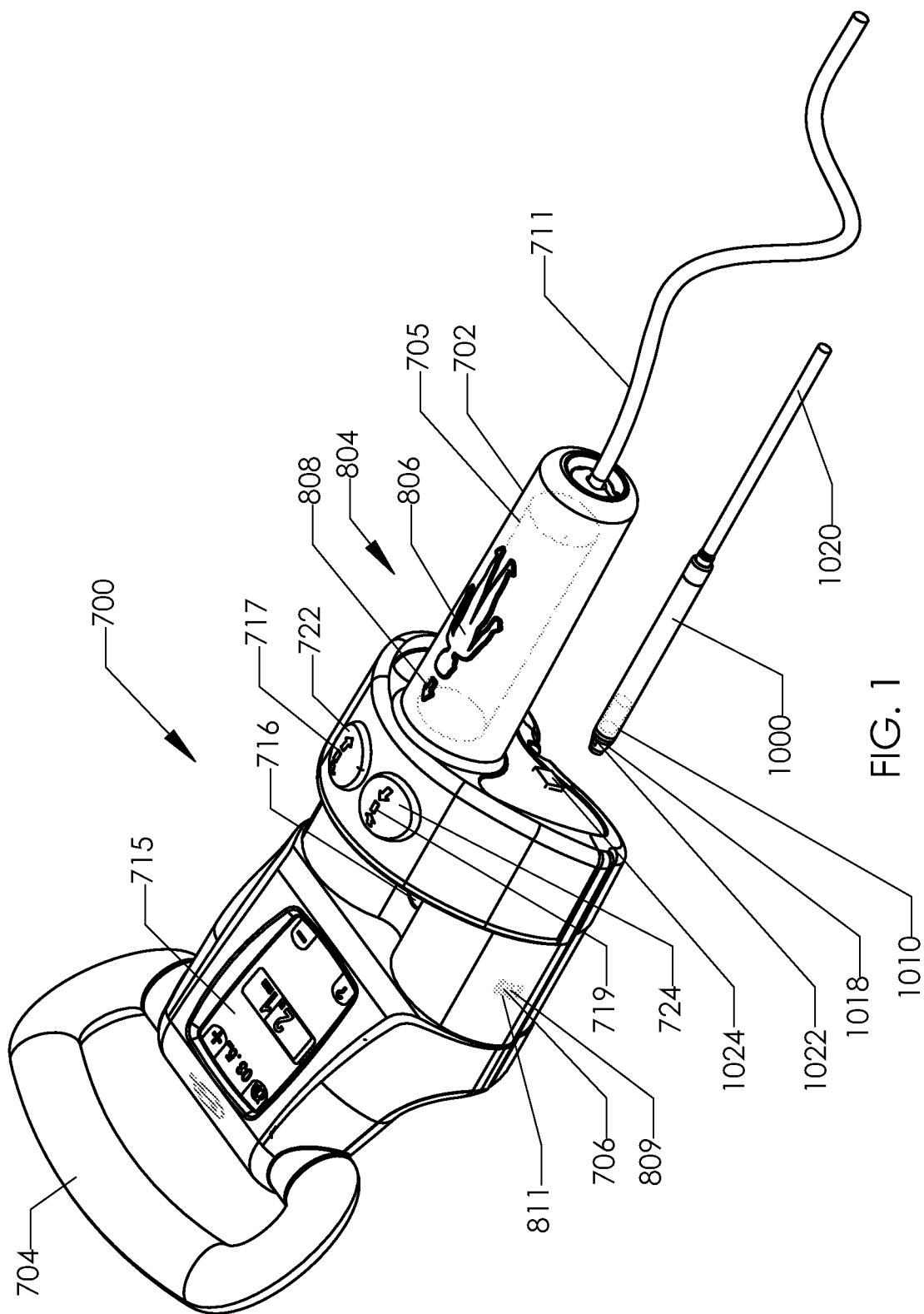
FIG. 1 illustrates an external adjustment device configured to operate a distraction device.
Figure 2:
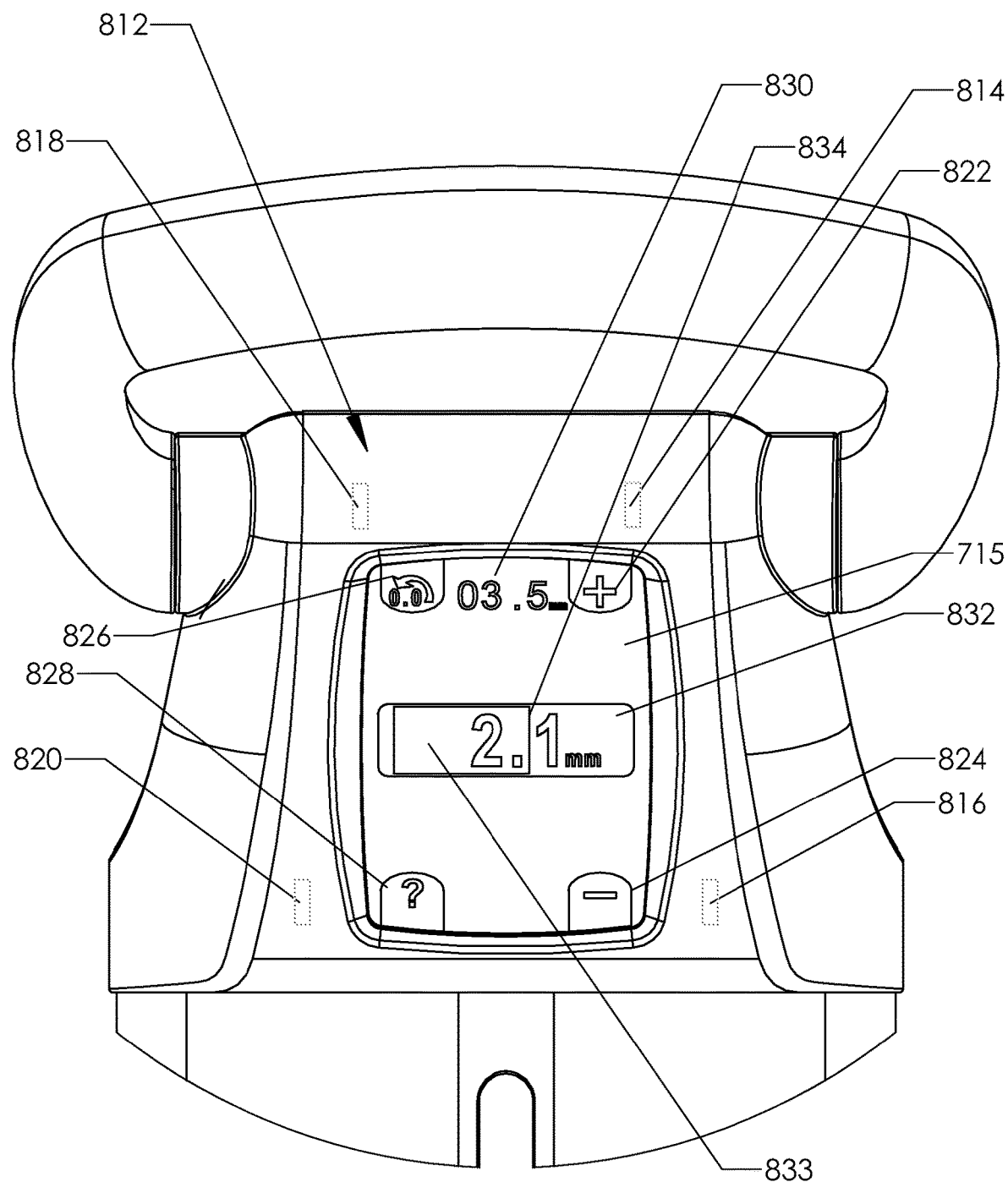
FIG. 2 illustrates a detailed view of the display and control panel of the external adjustment device.
Figure 3:
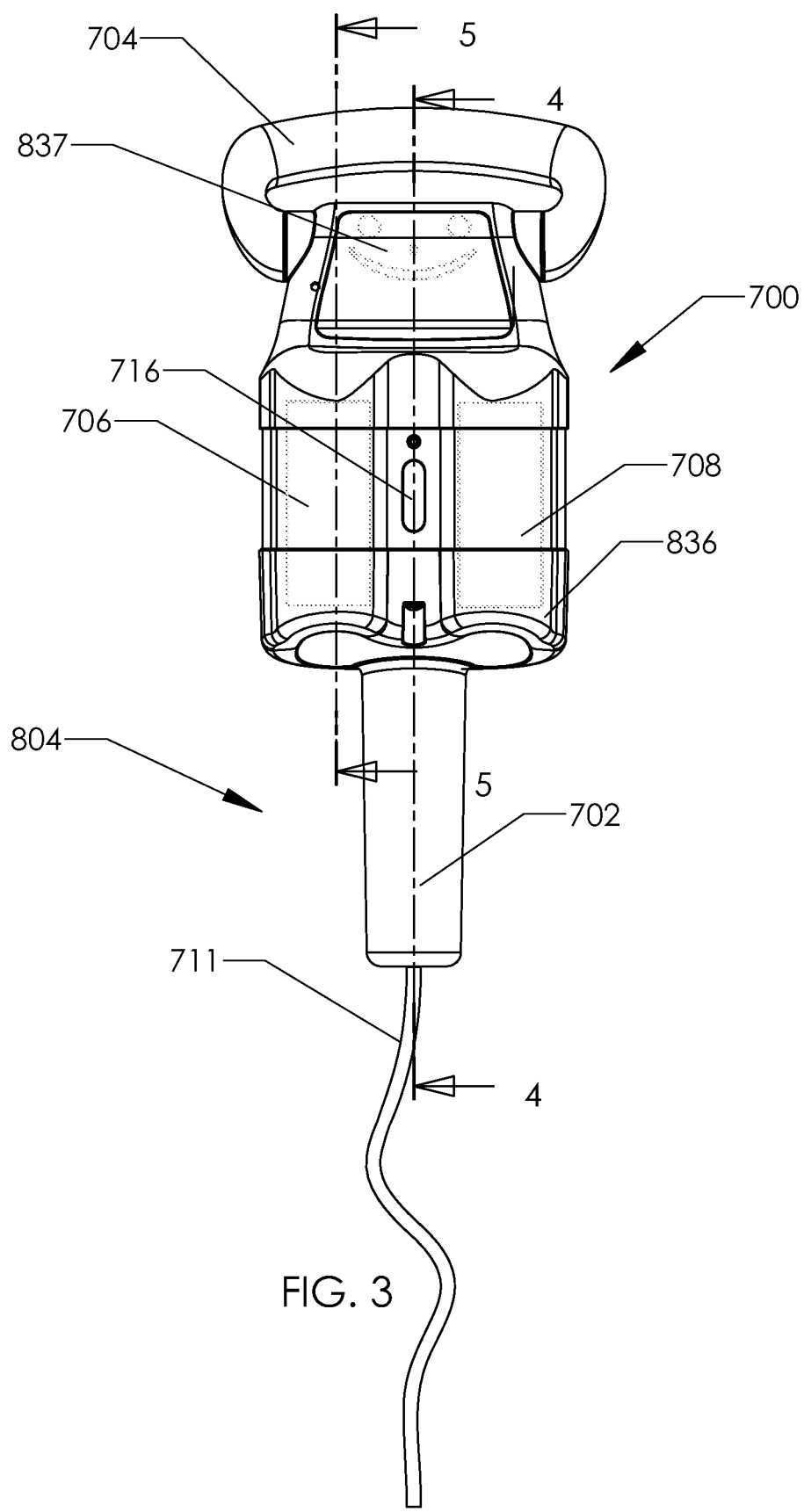
FIG. 3 illustrates the lower or underside surfaces of the external adjustment device.

FIGS. 1-3 illustrate an external adjustment device 700 that is configured for adjusting a distraction device 1000. The distraction device 1000 may include any number of distraction devices such as those disclosed in U.S. patent application Ser. Nos. 12/121,355, 12/250,442, 12/391,109, 11/172,678 which are incorporated by reference herein. The distraction device 1000 generally includes a rotationally mounted, internal permanent magnet 1010 that rotates in response to the magnetic field applied by the external adjustment device 700. Rotation of the magnet 1010 in one direction effectuates distraction while rotation of the magnet 1010 in the opposing direction effectuates retraction, external adjustment device 700 may be powered by a rechargeable battery or by a power cord 711. The external adjustment device 700 includes a first handle 702 and a second handle 704. The second handle 704 is in a looped shape, and can be used to carry the external adjustment device 700. The second handle 704 can also be used to steady the external adjustment device 700 during use. Generally, the first handle 702 extends linearly from a first end of the external adjustment device 700 while the second handle 704 is located at a second end of the external adjustment device 700 and extends substantially off axis or is angled with respect to the first handle 702. In one embodiment, the second handle 704 may be oriented substantially perpendicular relative to the first handle 702 although other The first handle 702 contains the motor 705 that drives a first external magnet 706 and a second external magnet 708 as best seen in FIG. 3, via gearing, belts and the like. On the first handle 702 is an optional orientation image 804 comprising a body outline 806 and an optional orientation arrow 808 that shows the correct direction to place the external adjustment device 700 on the patient's body, so that the distraction device is operated in the correct direction. While holding the first handle 702, the operator presses with his thumb the distraction button 722, which has a distraction symbol 717, and is a first color, for example green. This distracts the distraction device 1000. If the distraction device 1000 is over-distracted and it is desired to retract, or to lessen the distraction of the device 1000, the operator presses with his thumb the retraction button 724 which has a retraction symbol 719.

Distraction turns the magnets 706, 708 one direction and retraction turns the magnets 706, 708 in the opposite direction. Magnets 706, 708 have stripes 809 that can be seen in window 811. This allows easy identification of whether the magnets 706, 708 are stationary or turning, and in which direction they are turning. This allows quick trouble shooting by the operator of the device. The operator can determine the point on the patient where the magnet of the distraction device 1000 is implanted, and can then put the external adjustment device 700 in correct location with respect to the distraction device 1000, by marking the corresponding portion of the skin of the patient, and then viewing this spot through the alignment window 716 of the external adjustment device 700.

A control panel 812 includes several buttons 814, 816, 818, 820 and a display 715. The buttons 814, 816, 818, 820 are soft keys, and able to be programmed for an array of different functions. In one configuration, the buttons 814, 816, 818, 820 have corresponding legends which appear in the display. To set the length of distraction to be performed on the distraction device 1000, the target distraction length 830 is adjusted using an increase button 814 and a decrease button 816. The legend with a green plus sign graphic 822 corresponds to the increase button 814 and the legend with a red negative sign graphic 824 corresponds to the decrease button 816. It should be understood that mention herein to a specific color used for a particular feature should be viewed as illustrative. Other colors besides those specifically recited herein may be used in connection with the inventive concepts described herein. Each time the increase button 814 is depressed, it causes the target distraction length 830 to increase 0.1 mm. Each time the decrease button 816 is depressed it causes the target distraction length 830 to decrease 0.1 mm. Of course, other decrements besides 0.1 mm could also be used. When the desired target distraction length 830 is displayed, and the external adjustment device 700 is correctly placed on the patient, the operator then holds down the distraction button 722 and the External Distraction Device 700 operates, turning the magnets 706, 708, until the target distraction length 830 is achieved. Following this, the external adjustment device 700 stops. During the distraction process, the actual distraction length 832 is displayed, starting at 0.0 mm and increasing until the target distraction length 830 is achieved. As the actual distraction length 832 increases, a distraction progress graphic 834 is displayed. For example a light colored box 833 that fills with a dark color from the left to the right. In FIG. 2, the target distraction length 830 is 3.5 mm, and 2.1 mm of distraction has occurred, 60% of the box 833 of the distraction progress graphic 834 is displayed. A reset button 818 corresponding to a reset graphic 826 can be pressed to reset one or both of the numbers back to zero. An additional button 820 can be assigned for other functions (help, data, etc.). This button can have its own corresponding graphic 828. Alternatively, a touch screen can be used, for example capacitive or resistive touch keys. In this embodiment, the graphics/legends 822, 824, 826, 828 may also be touch keys, replacing or augmenting the buttons 814, 816, 818, 820. In one particular embodiment, touch keys at 822, 824, 826, 828 perform the functions of buttons 814, 816, 818, 820 respectively, and the buttons 814, 816, 818, 820 are eliminated.

The two handles 702, 704 can be held in several ways. For example the first handle 702 can be held with palm facing up while trying to find the location on the patient of the implanted magnet of the distraction device 1000. The fingers are wrapped around the handle 702 and the fingertips or mid-points of the four fingers press up slightly on the handle 702, balancing it somewhat. This allows a very sensitive feel that allows the magnetic field between the magnet in the distraction device 1000 and the magnets 706, 708 of the external adjustment device 700 to be more obvious, During the distraction of the patient, the first handle 702 may be held with the palm facing down, allowing the operator to push the device down firmly onto the patient, to minimize the distance between the magnets 706, 708 of the external adjustment device and the magnet 1010 of the distraction device 1000, thus maximizing the torque coupling. This is especially appropriate if the patient is large or somewhat obese. The second handle 704 may be held with the palm up or the palm down during the magnet sensing operation and the distraction operation, depending on the preference of the operator.

FIG. 3 illustrates the underside or lower surface of the external adjustment device 700. At the bottom of the external adjustment device 700, the contact surface 836 may be made of material of a soft durometer, such as elastomeric material, for example PEBAX® or Polyurethane. This allows for anti-shock to protect the device 700 if it is dropped. Also, if placing the device on patient's bare skin, materials of this nature do not pull heat away from patient as quickly, and so they "don't feel as cold" as hard plastic or metal. The handles 702, 704 may also have similar material covering them, in order to act as non-slip grips.

FIG. 3 also illustrates child friendly graphics 837, including the option of a smiley face. Alternatively this could be an animal face, such as a teddy bear, a horsey or a bunny rabbit. A set of multiple faces can be removable and interchangeable to match the likes of various young patients. In addition, the location of the faces on the underside of the device, allows the operator to show the faces to a younger child, but keep it hidden from an older child, who may not be so amused. Alternatively, sock puppets or decorative covers featuring human, animal or other characters may be produced so that the device may be thinly covered with them, without affecting the operation of the device, but additionally, the puppets or covers may be given to the young patient after a distraction procedure is performed. It is expected that this can help keep a young child more interested in returning to future procedures.

Figures 4, 5:
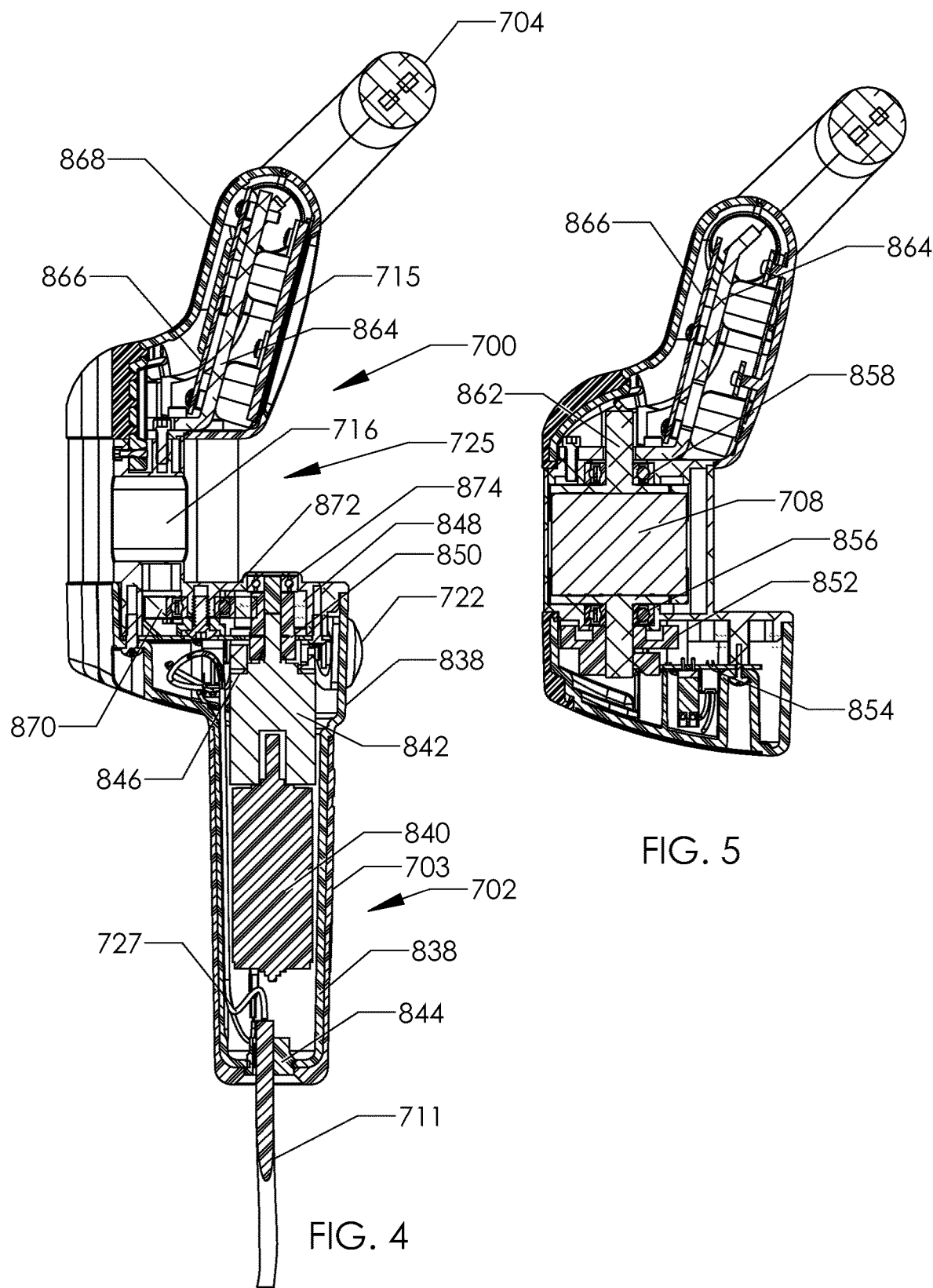
FIG. 4 illustrates a sectional view of the external adjustment device taken along line 4-4 of FIG. 3.
FIG. 5 illustrates a sectional view of the external adjustment device taken along line 5-5 of FIG. 3.

FIGS. 4 and 5 are sectional views that illustrate the internal components of the external adjustment device 700 taken along various centerlines. FIG. 4 is a sectional view of the external adjustment device 700 taken along the line 4-4 of FIG. 3. FIG. 5 is a sectional view of the external adjustment device 700 taken along the line 5-5 of FIG. 3. The external adjustment device 700 comprises a first housing 868, a second housing 838 and a central magnet section 725. First handle 702 and second handle 704 include grip 703 (shown on first handle 702). Grip 703 may be made of an elastomeric material and may have a soft feel when gripped by the hand. The material may also have a tacky feel, in order to aid firm gripping. Power is supplied via power cord 711, which is held to second housing 838 with a strain relief 844. Wires 727 connect various electronic components including motor 840 which rotates magnets 706, 708 via gear box 842, output gear 848, center gear 870 respectively, center gear 870 rotating two magnet gears 852, one on each magnet 706, 708 (one such gear 852 is illustrated in FIG. 5). Output gear 848 is attached to motor output via coupling 850, and both motor 840 and output gear 848 are secured to second housing 838 via mount 846. Magnets 706, 708 are held within magnet cups 862. Magnets and gears are attached to bearings 872, 874, 856, 858, which aid in low friction rotation. Motor 840 is controlled by motor printed circuit board (PCB) 854, while the display is controlled by display printed circuit board (PCB) 866 (FIG. 4). Display PCB 866 is attached to frame 864.

Figure 6:
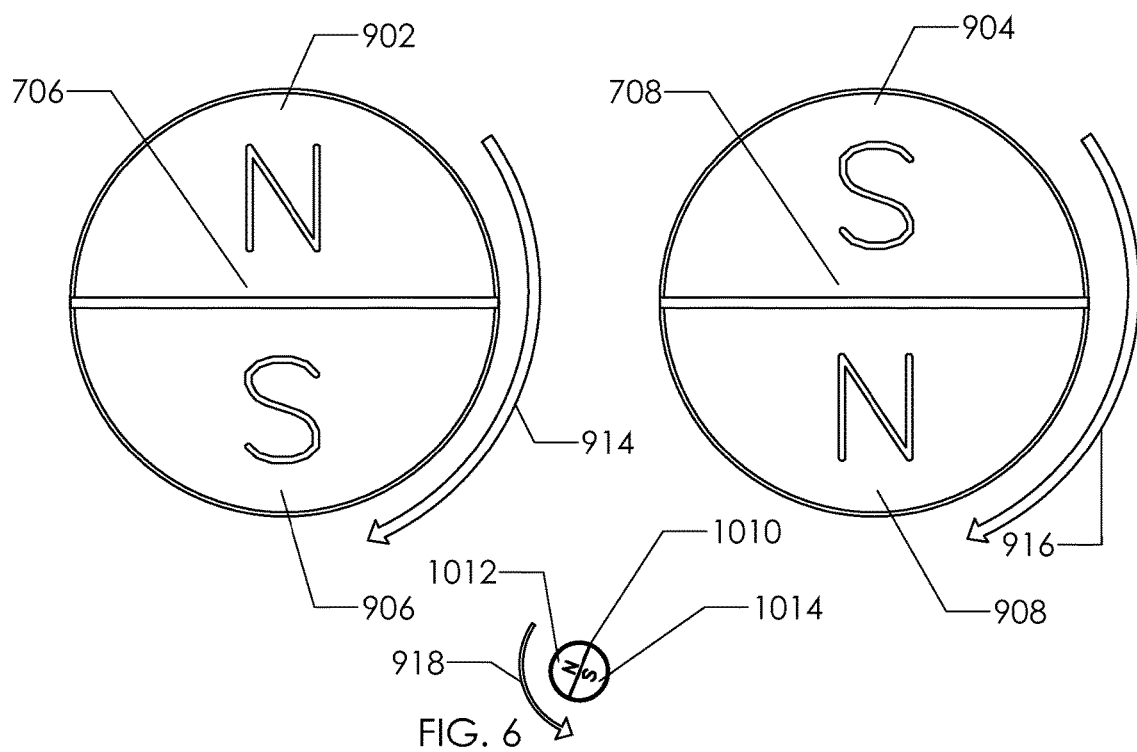
FIG. 6 schematically illustrates the orientation of the magnets of the external adjustment device while driving an implanted magnet of a distraction device.
Figure 7:
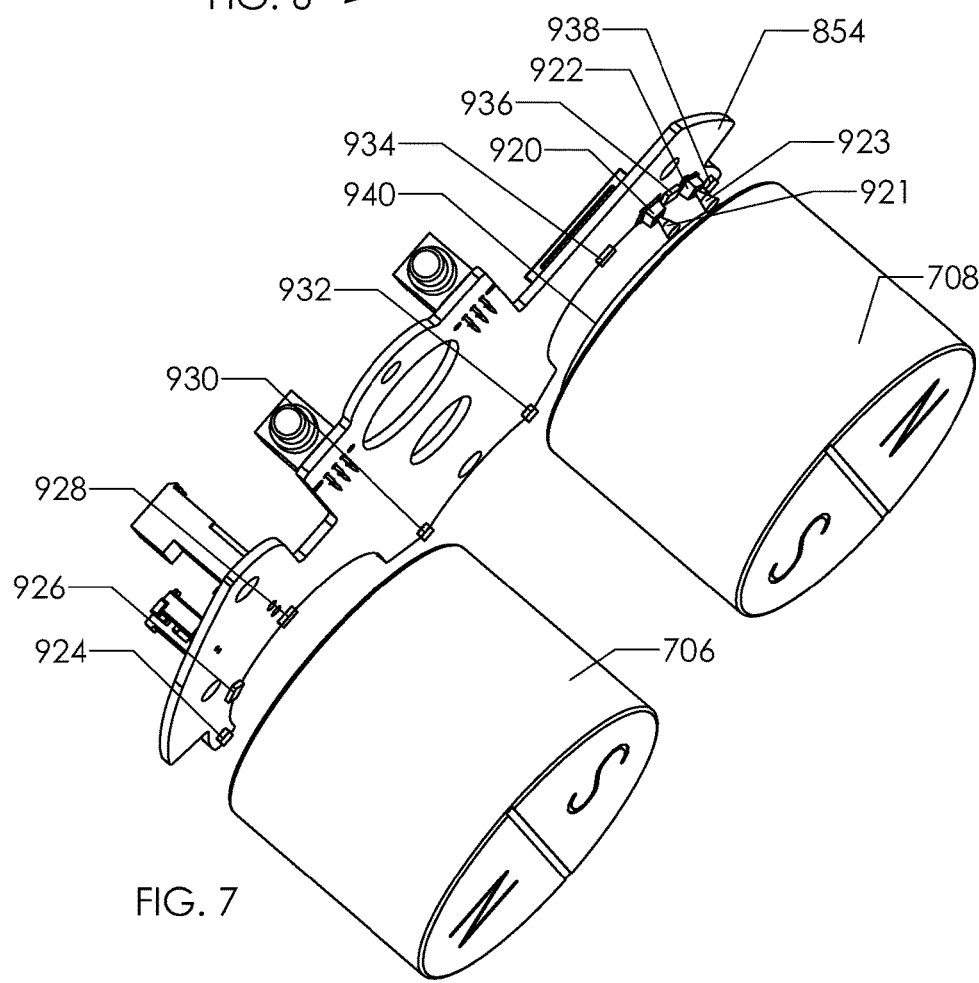
FIG. 7 illustrates various sensors connected to a printed circuit board of the external adjustment device.
Figure 8:
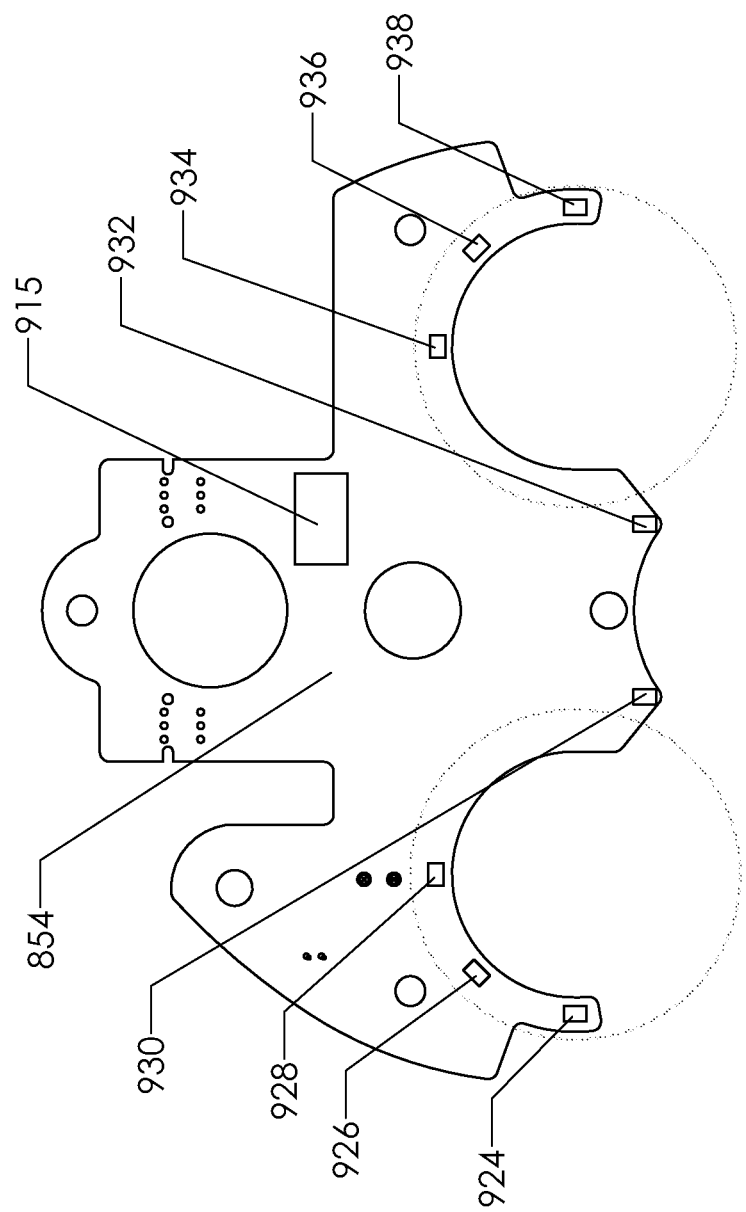
FIG. 8 illustrates a view of the clock positions of Hall effect sensors on the printed circuit board of the external adjustment device.

FIG. 6 illustrates the orientation of poles of the first and second external magnets 706, 708 and the implanted magnet 1010 of the distraction device 1000 during a distraction procedure. For the sake of description, the orientations will be described in relation to the numbers on a clock. First external magnet 706 is turned (by gearing, belts, etc.) synchronously with second external magnet 708 so that north pole 902 of first external magnet 706 is pointing in the twelve o'clock position when the south pole 904 of the second external magnet 708 is pointing in the twelve o'clock position. At this orientation, therefore, the south pole 906 of the first external magnet 706 is pointing is pointing in the six o'clock position while the north pole 908 of the second external magnet 708 is pointing in the six o'clock position. Both first external magnet 706 and second external magnet 708 are turned in a first direction as illustrated by respective arrows 914, 916. The rotating magnetic fields apply a torque on the implanted magnet 1010, causing it to rotate in a second direction as illustrated by arrow 918. Exemplary orientation of the north pole 1012 and south pole 1014 of the implanted magnet 1010 during torque delivery are shown in FIG. 6. When the first and second external magnets 706, 708 are turned in the opposite direction from that shown, the implanted magnet 1010 will be turned in the opposite direction from that shown. The orientation of the first external magnet 706 and the second external magnet 708 in relation to each other serves to optimize the torque delivery to the implanted magnet 1010. During operation of the external adjustment device 700, it is often difficult to confirm that the two external magnets 706, 708 are being synchronously driven as desired. Turning to FIGS. 7 and 8, in order to ensure that the external adjustment device 700 is working properly, the motor printed circuit board 854 comprises one or more encoder systems, for example photointerrupters 920, 922 and/or Hall effect sensors 924, 926, 928, 930, 932, 934, 936, 938. Photointerrupters 920, 922 each comprise an emitter and a detector. A radially striped ring 940 may be attached to one or both of the external magnets 706, 708 allowing the photointerrupters to optically encode angular motion. Light 921, 923 is schematically illustrated between the radially striped ring 940 and photointerrupters 920, 922.

Figure 9A:
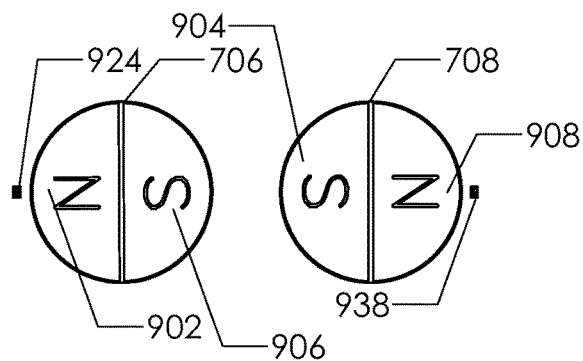
FIG. 9A illustrates a particular configuration of Hall effect sensors according to one embodiment.
Figure 9B:
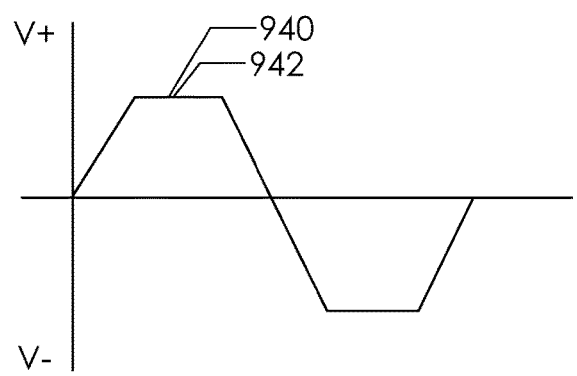
FIG. 9B illustrates output voltage of the Hall effect sensors of the configuration in FIG. 9A.
Figure 9C:
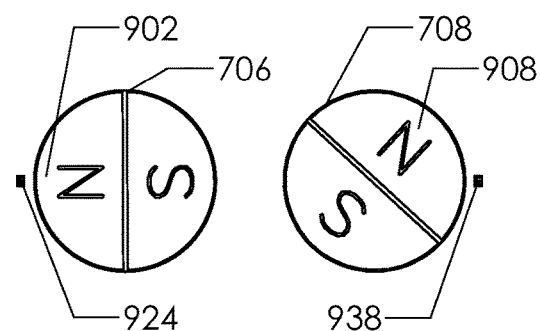
FIG. 9C illustrates the configuration of FIG. 9A, with the magnets in a nonsynchronous condition.
Figure 9D:
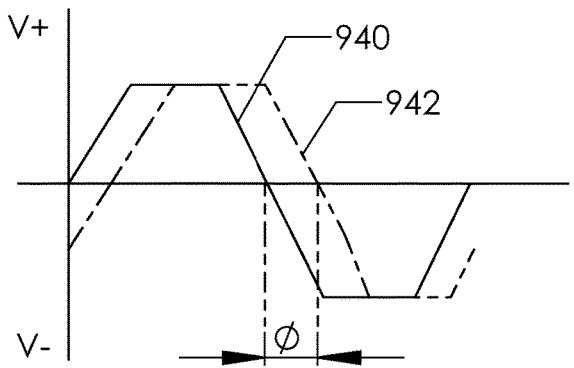
FIG. 9D illustrates the output voltage of the Hall effect sensors of the configuration in FIG. 9C.

Independently, Hall effect sensors 924, 926, 928, 930, 932, 934, 936, 938 may be used as non-optical encoders to track rotation of one or both of the external magnets 706, 708. While eight (8) such Hall effect sensors are illustrated in FIG. 7 it should be understood that fewer or more such sensors may be employed. The Hall effect sensors are connected to the motor printed circuit board 854 at locations that allow the Hall effect sensors to sense the magnetic field changes as the external magnets 706, 708 rotate. Each Hall effect sensor 924, 926, 928, 930, 932, 934, 936, 938 outputs a voltage that corresponds to increases or decreases in the magnetic field. FIG. 9A indicates one basic arrangement of Hall effect sensors relative to sensors 924, 938. A first Hall effect sensor 924 is located at nine o'clock in relation to first external magnet 706. A second Hall effect sensor 938 is located at three o'clock in relation to second external magnet 708. As the magnets 706, 708 rotate correctly in synchronous motion, the first voltage output 940 of first Hall effect sensor 924 and second voltage output 942 of second Hall effect sensor have the same pattern, as seen in FIG. 9B, which graphs voltage for a full rotation cycle of the external magnets 706, 708. The graph indicates a sinusoidal variance of the output voltage, but the clipped peaks are due to saturation of the signal. Even if Hall effect sensors used in the design cause this effect, there is still enough signal to compare the first voltage output 940 and the second voltage output 942 over time. If either of the two Hall effect sensors 924, 938 does not output a sinusoidal signal during the operation or the external adjustment device 700, this demonstrates that the corresponding external magnet has stopped rotating, for example due to adhesive failure, gear disengagement, etc. FIG. 9C illustrates a condition in which both the external magnets 706, 708 are rotating at the same approximate angular speed, but the north poles 902, 908 are not correctly synchronized. Because of this, the first voltage output 940 and second voltage output 942 are now out-of-phase, and exhibit a phase shift (e). These signals are processed by a processor 915 and an error warning is displayed on the display 715 of the external adjustment device 700 so that the device may be resynchronized.

Figure 10A:
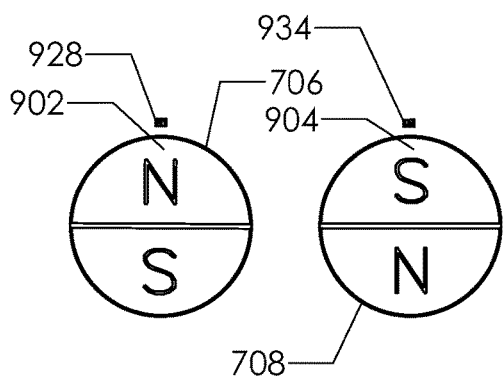
FIG. 10A illustrates a particular configuration of Hall effect sensors according to another embodiment.
Figure 10B:
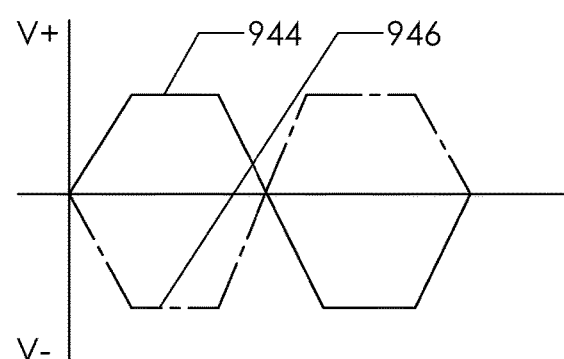
FIG. 10B illustrates the output voltage of the Hall effect sensors of the configuration in FIG. 10A.

If independent stepper motors are used, the resynchronization process may simply be one of reprogramming, but if the two external magnets 706, 708 are coupled together, by gearing or belt for example, then a mechanical rework may be required. An alternative to the Hall effect sensor configuration of FIG. 9A is illustrated in FIG. 10A. In this embodiment, a third Hall effect sensor 928 is located at twelve o'clock in relation to the first external magnet 706 and a fourth Hall effect sensor 934 is located at twelve o'clock in relation to the second external magnet 708. With this configuration, the north pole 902 of the first external magnet 706 should be pointing towards the third Hall effect sensor 928 when the south pole 904 of the second external magnet 708 is pointing towards the fourth Hall effect sensor 934. With this arrangement, the third Hall effect sensor 928 outputs a third output voltage 944 and the fourth Hall effect sensor 934 outputs a fourth output voltage 946 (FIG. 0.10B). The third output voltage 944 is by design out of phase with the fourth output voltage 946. An advantage of the Hall effect sensor configuration of FIG. 9A is that the each sensor has a larger distance between it and the opposite magnet, for example first Hall effect sensor 924 in comparison to second external magnet 708, so that there is less possibility of interference. An advantage to the Hall effect sensor configuration of FIG. 10A is that it may be possible to make a more compact external adjustment device 700 (less width). The out-of-phase pattern of FIG. 10B can also be analyzed to confirm magnet synchronicity.

Returning to FIGS. 7 and 8, additional Hall effect sensors 926, 930, 932, 936 are shown. These additional sensors allow additional precision to the rotation angle feedback of the external magnets 706, 708 of the external adjustment device 700. Again, the particular number and orientation of Hall effect sensors may vary. In place of the Hall effect sensors, magnetoresistive encoders may also be used.

In still another embodiment, additional information may be processed by processor 915 and may be displayed on display 715. For example, distractions using the external adjustment device 700 may be performed in a doctor's office by medical personnel, or by patients or members of patient's family in the home. In either case, it may be desirable to store information from each distraction session that can be accessed later. For example, the exact date and time of each distraction, and the amount of distraction attempted and the amount of distraction obtained. This information may be stored in the processor 915 or in one or more memory modules (not shown) associated with the processor 915. In addition, the physician may be able to input distraction length limits, for example the maximum amount that can be distracted at each session, the maximum amount per day, the maximum amount per week, etc. The physician may input these limits by using a secure entry using the keys or buttons of the device, that the patient will not be able to access.

Returning to FIG. 1, in some patients, it may be desired to place a first end 1018 of the distraction device 1000 proximally in the patient, or towards the head, and second end 1020 of the distraction device 1000 distally, or towards the feet. This orientation of the distraction device 1000 may be termed antegrade. In other patients, it may be desired to orient the distraction device 1000 with the second end 1020 proximally in the patient and the first end 1018 distally. In this case, the orientation of the distraction device 1000 may be termed retrograde. In a distraction device 1000 in which the magnet 1010 rotates in order to turn a screw within a nut, the orientation of the distraction device 1000 being either antegrade or retrograde in patient could mean that the external adjustment device 700 would have to be placed in accordance with the orientation image 804 when the distraction device 1000 is placed antegrade, but placed the opposite of the orientation image 804 when the distraction device 1000 is placed retrograde. Alternatively, software may be programmed so that the processor 915 recognizes whether the distraction device 1000 has been implanted antegrade or retrograde, and then turns the magnets 706, 708 in the appropriate direction when the distraction button 722 is placed.

For example, the motor 705 would be commanded to rotate the magnets 706, 708 in a first direction when distracting an antegrade placed distraction device 1000, and in a second, opposite direction when distracting a retrograde placed distraction device 1000. The physician may, for example, be prompted by the display 715 to input using the control panel 812 whether the distraction device 1000 was placed antegrade or retrograde. The patient may then continue to use the same external adjustment device 700 to assure that the motor 705 turns the magnets 706, 708 in the proper directions for both distraction and retraction. Alternatively, the distraction device may incorporate an RFID chip 1022 which can be read and written to by an antenna 1024 on the external adjustment device 700. The position of the distraction device 1000 in the patient (antegrade or retrograde) is written to the RFID chip 1022, and can thus be read by the antenna 1024 of any external adjustment device 700, allowing the patient to get correct distractions or retractions, regardless of which external adjustment device 700 is used.

While embodiments have been shown and described, various modifications may be made without departing from the scope of the inventive concepts disclosed herein. The invention(s), therefore, should not be limited, except to the following claims, and their equivalents.

What is claimed is:
1. An external adjustment device comprising:
   at least one permanent magnet configured for rotation about an axis;
   a handle;
   a motor mounted inside the handle;

a first button located in the proximity to the handle, the first button configured to be operated by the thumb of a hand that grips the handle, wherein the first button is configured to actuate the motor causing the at least one permanent magnet to rotate about the axis in a first direction;

a first magnetic sensor configured to sense a magnetic field of the at least one permanent magnet and communicate an output of a first time-variable voltage based at least in part on a time-variable strength of the sensed magnetic field corresponding to the rotation of the at least one permanent magnet.

2. The external adjustment device of claim 1, further comprising a second button located in proximity to the first button, the second button configured to actuate the motor causing the at least one permanent magnet to rotate about the axis in a second direction.

3. The external adjustment device of claim 1, further comprising a control panel having a plurality of buttons and a display.

4. The external adjustment device of claim 3, wherein the plurality of buttons comprise a target distraction increase button and a target distraction decrease button.

5. The external adjustment device of claim 3, wherein the plurality of buttons comprises at least one touch key.

6. The external adjustment device of claim 1, wherein the at least one permanent magnet is rotatably disposed in a housing having a window therein and wherein the at least one permanent magnet contains a plurality of stripes visible via the window.

7. The external adjustment device of claim 1, wherein the at least one permanent magnet comprises two permanent magnets.

8. The external adjustment device of claim 1, further comprising an orientation image on the handle.

9. The external adjustment device of claim 1, wherein the handle comprises a looped shape.

10. The external adjustment device of claim 1, comprising a second magnetic sensor configured to sense a change in a magnetic field of the at least one permanent magnet and to output a voltage based at least partially on strength of the magnetic field.

11. An external adjustment device comprising:
a at least one permanent magnet configured for rotation about an axis;
a motor configured for rotating the at least one permanent magnet about the axis;
a first handle;
a second handle;
a first drive button located in the proximity to one of the first handle or the second handle, the first drive button configured to be operated by the thumb of a hand that grips the one of the first handle or second handle, the first drive button configured to actuate the motor causing the at least one permanent magnet to rotate about the axis in a first direction;
a first magnetic sensor configured to sense a magnetic field of the at least one permanent magnet and communicate an output of a first time-variable voltage based at least in part on a time-variable strength of the sensed magnetic field corresponding to the rotation of the at least one permanent magnet.

12. The external adjustment device of claim 11, comprising a second magnetic sensor configured to sense a change in a magnetic field of the at least one permanent magnet and output a voltage based at least in part on a strength of the magnetic field.

13. The external adjustment device of claim 12, further comprising a processor configured to compare respective output voltages from the first and second magnetic sensors.

14. The external adjustment device of claim 12, further comprising a second button located in proximity to the first button, the second button configured to actuate the motor causing the at least one permanent magnet to rotate about the axis in a second direction.

15. The external adjustment device of claim 11, further comprising: a distraction device configured for implantation within a subject; and
a processor disposed in the external adjustment device and configured to actuate the motor causing the at least one permanent magnet to rotate about the axis in a first direction when the distraction device is implanted an antegrade orientation and in a second direction when the distraction device is implanted in a retrograde orientation.

16. The external adjustment device of claim 15, further comprising a read/write RFD chip disposed on the distraction device.

17. The external adjustment device of claim 16, wherein the external adjustment device comprises an antenna configured to receive and transmit data to the read/write RFID chip.

18. The external adjustment device of claim 17, wherein the data comprises the orientation of the distraction device.

19. The external adjustment device of claim 15, wherein the processor is configured to receive instructions from a user as the antegrade or retrograde orientation of the distraction device.

* * * * *